US012748977B2

(12) United States Patent
Richards

(10) Patent No.: US 12,748,977 B2
(45) Date of Patent: Sep. 29, 2026

(54) SYSTEM AND METHOD FOR HUMAN ACTIVITY RECOGNITION

(71) Applicant: Prolaio, Inc., Scottsdale, AZ (US)

(72) Inventor: Dylan Richards, Chicago, IL (US)

(73) Assignee: Prolaio, Inc., Scottsdale, AZ (US)

( * ) Notice: Subject to any disclaimer, the term of this patent is extended or adjusted under 35 U.S.C. 154(b) by 425 days.

(21) Appl. No.: 18/234,725

(22) Filed: Aug. 16, 2023

(65) Prior Publication Data

US 2024/0062065 A1 Feb. 22, 2024

Related U.S. Application Data

(60) Provisional application No. 63/399,002, filed on Aug. 18, 2022.

(51) Int. Cl.
*G06N 3/084* (2023.01)
*G06N 3/045* (2023.01)
*G16H 10/20* (2018.01)

(52) U.S. Cl.
CPC ............. *G06N 3/084* (2013.01); *G06N 3/045* (2023.01); *G16H 10/20* (2018.01)

(58) Field of Classification Search
None
See application file for complete search history.

(56) References Cited

U.S. PATENT DOCUMENTS

2020/0062275 A1 2/2020 Higgins et al.
2021/0020293 A1* 1/2021 Richards ................ G16H 20/30
2021/0279554 A1* 9/2021 Ibtehaz .................. G16H 20/30
2022/0130109 A1 4/2022 Arbabian et al.

FOREIGN PATENT DOCUMENTS

WO WO-2016149831 A1 * 9/2016 ............. A61B 5/397
WO 2021011381 A1 1/2021

OTHER PUBLICATIONS

Li et al, Human Motion Pattern Recognition and Feature Extraction, Jul. 2022, Micromachines 2022, 13, p. 1205 (Year: 2022).*
Rueda et al, Convolutional Neural Networks for Human Activity Recognition Using Body-Worn Sensors, 2018, Informatics 2018, 5, p. 26 (Year: 2018).*
Bhuiyan et al, A Robust Feature Extraction Model for Human Activity Characterization Using 3-Axis Accelerometer and Gyroscope Data, 2020, Sensors 2020, 20, p. 6990 (Year: 2020).*
Erdas et al, Integrating Features for Accelerometer-Based Activity Recognition, 2016, Procedia Computer Science 98, pp. 522-527 (Year: 2016).*

(Continued)

*Primary Examiner* — Gregory Lultschik
(74) *Attorney, Agent, or Firm* — HONIGMAN LLP

(57) ABSTRACT

In aspects, the present approaches allow neural networks to be taught to understand patterns of human behavior without the need of expert data labeling or laboratory studies. First and second neural networks are trained to understand these patterns without labeling. Once trained, the neural networks can be deployed with a trained classifier to determine or classify human activity based upon received sensor inputs.

27 Claims, 12 Drawing Sheets

(56) References Cited

OTHER PUBLICATIONS

International Search Report and Written Opinion for International Patent Application No. PCT/US2023/030425, dated Nov. 9, 2023, 7 pages.
Deldari et al., "Cocoa: Cross modality contrastive learning for sensor data." Proceedings of the ACM on Interactive, Mobile, Wearable and Ubiquitous Technologies 6.3 (2022), 1-28.
Han et al., "Matchnet: Unifying feature and metric learning for patch-based matching" Proceedings of the IEEE confernece on computer vision and pattern recognition, 2025, pp. 3279-3286.
Arandjelovic et al., "Look, listen and learn" Proceedings of the IEEE international conference on computer vision, 2017, pp. 609-617.
Jain et al., "ColloSSL: Collaborative self-supervised learning for human activity recognition" Proceedings of the ACM on Interactive, Mobile, Wearable and Ubiquitous Technologies 6(1), 2022, pp. 1-28.
Sama et al., "A Double Closed Loop to Enhance the Quality of Life of Parkinson's Disease Patients: REMPARK system" Studies in Health Technology and Informatics, vol. 27, Jan. 1, 2024.
EP Search Report dated Jun. 8, 2026 from corresponding EP Patent Application No. 23855445.5.
Yu et al., "A Novel Hybrid Deep Neural Network to Predict Pre-impact Fall for Older People Based on Wearable Inertial Sensors" Frontiers in Bioengineering and Biotechnology, vol. 8, Article 63, Feb. 12, 2020, pp. 1-10.
Japanese Office Action and English translation dated Jun. 30, 2026 from corresponding Japanese Patent Application No. 2025-508957.

* cited by examiner

SYSTEM AND METHOD FOR HUMAN ACTIVITY RECOGNITION

CROSS REFERENCE TO RELATED APPLICATION

This application claims the benefit of priority of U.S. Provisional Application 63/399,002, filed Aug. 18, 2022, which is incorporated by reference herein in its entirety.

TECHNICAL FIELD

The field of the invention relates to training neural networks to understand patterns of human behavior and/or using these trained neural networks in various applications.

BACKGROUND

Human activity recognition (HAR) is an area of machine learning (ML) research. The HAR field seeks to classify or recognize the activity of a human from available sensor data such as video signals or wearable sensor accelerometer signals. HAR has value in many fields, including health care, where results could be useful in monitoring health status outside the acute care environment, or measuring the impact of Deep neural network architectures have been utilized in many machine learning domains. However, deep neural networks have not dominated in the HAR field as in other fields.

Deep neural networks need vast amounts of data to successfully train. Ideally, this data is hand-labelled by human experts. Particularly in the image recognition area, state of the art models are created with cameras and human annotation providing the necessary training data.

Compared to the amount of image, text, and audio data publicly available, the amount of publicly available wearable sensor data is practically zero. Additionally, the labelling of wearable sensor data cannot easily be done by non-experts, unlike that of images or audio data. Data from worn accelerometers for example cannot be directly recognized by humans tasked with labeling the data, in contrast to labeling objects in images or types of sounds. This has led to the need for activity recognition studies to be performed in a laboratory setting where data from human subjects is directly collected, such that the researchers dictate which activities the subjects must perform, so that the data can be labeled a priori as the dictated activity, rather than trying to recognize the raw accelerometer data.

As such, laboratory studies typically result in artificial movements being taken by the human subjects, and the labelling of human behavior becomes very difficult. Human activity is inherently hierarchical. Any complex activity can always be broken down into simpler motions, which themselves can be further broken down or sub-categorized. Activity recognition studies in laboratories by expediency will pick some level on the activity hierarchy which they will label and will simply discard all other hierarchical activity labels because it is too difficult to capture. This leads to almost every activity recognition study defining different activity classes to recognize, with varying levels of overlap between other studies. As a result, it is difficult to amass sufficient data to leverage the power of deep neural network learning to improve activity recognition based on movement sensor data from wearable sensors.

There is a need for a method to enable use of deep neural networks to learn activity recognition other than by brute-force human labeling from in-clinic artificial activity studies. There is a need for a network architecture that exhibits improved computational abilities to learn relevant aspects of human activity to facilitate better recognition, by zeroing in on relevant movement features at all levels of movement hierarchy that are available in the data.

BRIEF DESCRIPTION OF THE DRAWINGS

For a more complete understanding of the disclosure, reference should be made to the following detailed description and accompanying drawings wherein.

DETAILED DESCRIPTION

Figure 1A:
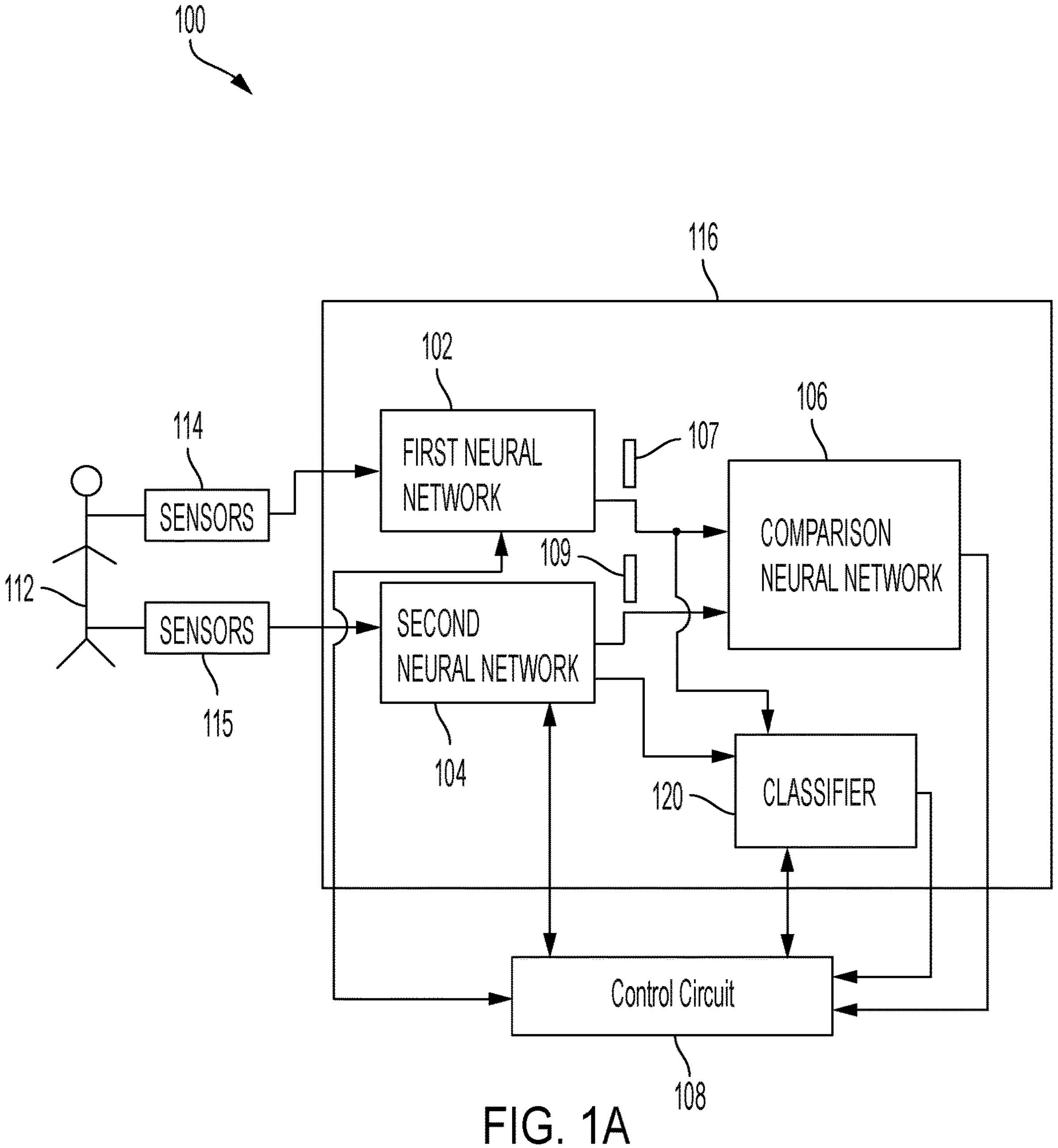
FIG. 1A comprises a diagram of a system as configured in accordance with various embodiments of these teachings.

Advantageously, the approaches provided herein allow deep neural networks to be taught to understand patterns of human behavior without the need of expert data labeling or laboratory studies. Generally speaking, the approaches provided include a neural network, which accepts a time window (e.g., 1 minute) of wearable sensor signals (e.g., from accelerometers, gyroscopes, etc.) and produces a rich, hierarchical description of every second of the input signal. The description is not directly understandable by humans but can easily be used with a small amount of human labelled data to produce any level of activity classification as desired. As described elsewhere herein, this neural network is trained and once trained is used in various applications to perform various actions.

In other aspects, the approaches provided herein use a large amount of data from two or more simultaneously worn wearable sensors to train a neural network to understand human activity. Compared to collecting labelled laboratory data, it is relatively easy to provide a group of people with multiple wearable devices and have them collect data during their activities of daily living. For example, groups of subjects might wear a smartwatch on their wrist and a monitoring patch on their chest. Both of these devices would collect simultaneous accelerometer data.

If a person collects simultaneous data from two or more locations on the body, then the signals must be from the same activity. This avoids the need for labelled data to train a deep neural network because paired data is effectively "labeled" without needing to know the underlying activity class. Simultaneously collected data gathered in this way must be of the same activity class, whatever that activity class is, and if paired data is artificially mixed, then this mis-matched paired data cannot be of the exact same class.

In many of these embodiments, a first neural network is iteratively trained to obtain a first trained neural network and a second neural network is iteratively trained to obtain a second trained neural network. The training includes receiving a first set of wearable sensor data at the first neural network. The first neural network responsively produces a first feature vector, and the first wearable sensor data describes first physiological features of a human. Any labels in the first set of wearable sensor data are ignored.

The training further includes receiving a second set of second wearable sensor data at the second neural network. The second neural network responsively produces a second feature vector. The second wearable sensor data describes second physiological features of the human. Any labels in the second set of wearable sensor data are ignored. At least some of the first set of wearable sensor data and the second set of wearable sensor data are obtained from the same human activity of the same human occurring at the same time, time period, or time frame.

The training further comprises predicting at a comparison neural network whether the first feature vector from the first neural network and the second feature vector from the second neural network are matched or mis-matched. The first feature vector and second feature vector are determined to be matched when the first feature vector and the second feature vector are from the same human and taken at substantially the same time.

The training still further includes back propagating to the first neural network and the second neural network an error generated by a cost function that penalizes a failure to correctly determine whether the vectors are matched or mis-matched. The backpropagation is effective to independently update parameters of the first neural network and the second neural network, to optimize a generation of features by the first neural network and the second neural network and to optimize prediction success of the comparison neural network.

The first trained neural network is then deployed. At least one current human subject is monitored to obtain current wearable sensor data and the current wearable sensor data is applied to the first trained neural network to obtain a current feature vector.

A classifier is trained. At the trained classifier, the current feature vector is mapped to a classification representing one or more classes of activity. Based upon the classification, one or more actions are performed.

In one example, the action is quantifying health effects between at least a control group receiving a first intervention or no intervention and a test group receiving a second intervention in a clinical trial. In another example, the action includes determining possible health changes in the monitored human subject. In yet other examples, the action is issuing an alert to a clinician to investigate the health of the monitored human subject.

In yet another example, the action includes selectively controlling the actuation or deactivation of a device. In other examples, the action is controlling the operation or setting a parameter of a medical device associated with treating or monitoring the monitored human subject. In still another example, the action is controlling the operation or setting a parameter of a user electronic device associated with treating or monitoring the monitored human subject.

In other examples, the mapping utilizes known and labeled vectors from other monitored human subjects.

In aspects, the sensors are wrist sensors or chest sensors. Sensors are available and known in the art that can be worn by a person continuously throughout activities of daily living and record waveform data that characterizes the movement of the person, and often also data that characterize ambient conditions, cardiopulmonary function, temperature and more. Such waveforms can include accelerometer waveforms, gyroscopic waveforms, electrocardiographic (ECG) waveforms, photoplethysmographic (PPG) waveforms, impedance waveforms, electromyographic (EMG) waveforms, or electroencephalographic (EEG) waveforms. Such sensors can be wristwatch devices or adhesive band-daid-like devices. In other aspects, the user electronic device is a smartphone, a personal computer, a laptop, or a tablet. Other examples of sensors and user electronic devices are possible.

In other examples, the trained classifier comprises a random forest or a third neural network. Other examples are possible.

In yet other examples, the first neural network and the second neural network are trained at a central location. Training can occur at other locations as well.

In still other aspects, the comparison network comprises an ensemble of separate comparison networks with different time scales of a fixed input window size.

In others of these embodiments, a system of determining and implementing appropriate life-improving actions for humans includes a first neural network, a second neural network, and a comparison neural network. The comparison neural network is coupled to the first neural network and the second neural network.

The first neural network is configured to receive a first set of wearable sensor data and responsively produce a first feature vector. The first wearable sensor data describes first physiological features of a human. Any labels in the first set of wearable sensor data are ignored.

The second neural network is configured to receive a second set of second wearable sensor data. The second neural network responsively produces a second feature vector. The second wearable sensor data describes second physiological features of the human. Any labels in the second set of wearable sensor data are ignored.

At least some of the first set of wearable sensor data and the second set wearable sensor data are obtained from the same human activity of the same human occurring at the same time.

The comparison neural network is configured to predict whether the first feature vector from the first neural network and the second feature vector from the second neural network are matched or mis-matched. The first feature vector and second feature vector are determined to be matched when the first feature vector and the second feature vector are from the same human and taken at substantially the same time.

An error is back propagated to the first neural network and the second neural network. The error is generated by a cost function that penalizes a failure to correctly determine whether the vectors are matched or mis-matched. The back propagation is effective to independently update parameters of the first neural network and the second neural network to produce a first trained neural network and a second trained neural network.

The system further comprises a trained classifier and wearable sensors. The wearable sensors are worn by a current human subject.

The first trained neural network is deployed, and current wearable sensor data is obtained from the current human subject by the wearable sensors and applied to the first trained neural network to obtain a current feature vector. At the trained classifier, the current feature vector is mapped to a classification representing one or more classes of activity.

Based on the classification one or more actions are performed. In one example, the action is quantifying health effects between at least a control group receiving a first intervention or no intervention and a test group receiving a second intervention in a clinical trial. In another example, the action includes determining possible health changes in the monitored human subject. In yet other examples, the action is issuing an alert to a clinician to investigate the health of the monitored human subject.

In still another example, the action includes selectively controlling the actuation or deactivation of a device. In other examples, the action is controlling the operation or setting a parameter of a medical device associated with treating or monitoring the monitored human subject. In still another example, the action is controlling the operation or setting a parameter of a user electronic device associated with treating or monitoring the monitored human subject.

In other aspects the mapping utilizes known and labeled vectors from other monitored human subjects.

In examples, the wearable sensors are wrist sensors or chest sensors. Other examples of sensors are possible.

In other examples, the trained first neural network is deployed at a central location. In other example, the trained neural networks can be deployed at remote locations.

In still other examples, the training occurs at a central location. Training can occur at remote locations as well.

In aspects, the trained classifier comprises a random forest or a third neural network. Other examples are possible.

In still others of these embodiments, a system for training neural networks comprises a first neural network; a second neural network; a comparison neural network coupled to the first neural network and the second neural network; and a control circuit coupled to the first neural network, the second neural network, and the comparison neural network.

The control circuit is configured to obtain a first collection of samples of wearable sensor data from a plurality of humans with a first type of wearable sensor. The control circuit is further configured to obtain a second collection of samples of wearable sensor data from a plurality of humans with a second type of wearable sensor. At least some of said samples are matched to the same human and substantially the same time-window as samples of said first collection. The control circuit is further configured to train the first neural network to produce a first trained neural network by iteratively inputting samples from said first collection to said first neural network to generate features; inputting samples from said second collection to a second neural network to generate features; inputting features from said first neural network together with features from said second neural network to the comparison neural network that responsively predicts whether input samples were matched or mis-matched; and back propagating to the first neural network and the second neural network an error generated by a cost function that penalizes failure to correctly determine whether the input samples are matched or mis-matched, to change neural parameters of the first neural network and the second neural network independently, to optimize generation of features by the first neural network and by the second neural network that optimize prediction success of the comparison neural network.

In other aspects, the system further comprises a trained classifier. The first trained neural network is subsequently deployed and wearable sensor data from a monitored human subject is captured. The wearable sensor data is applied to the first neural network and the first neural network responsively generates a set of features responsive to a time-window of the wearable sensor data.

The trained classifier maps the generated features to one or more classes of activity in said time-window. Based on said classification, one or more actions are performed. In one example, the action is quantifying health effects between at least a control group receiving a first intervention or no intervention and a test group receiving a second intervention in a clinical trial. In another example, the action includes determining possible health changes in the monitored human subject. In yet other examples, the action is issuing an alert to a clinician to investigate the health of the monitored human subject.

In yet another example, the action includes selectively controlling the actuation or deactivation of a device. In other examples, the action is controlling the operation or setting a parameter of a medical device associated with treating or monitoring the monitored human subject. In still another example, the action is controlling the operation or setting a parameter of a user electronic device associated with treating or monitoring the monitored human subject.

In others of these embodiments, an approach of training a neural network includes obtaining a first collection of samples of wearable sensor data from a plurality of humans with a first wearable sensor. A second collection of samples of wearable sensor data is obtained from a plurality of humans with a second wearable sensor. At least some of said samples being matched to the same human and substantially the same time-window as samples of said first collection.

The first neural network is trained to produce a first trained neural network by iteratively: inputting samples from said first collection to said first neural network to generate features; inputting samples from said second collection to a second neural network to generate features; inputting features from said first neural network together with features from said second neural network to a comparison network that predicts whether input samples were matched or mis-matched; back propagating to said first neural network and said second neural network an error generated by a cost function that penalizes failure to correctly determine whether the input samples are matched or mis-matched, to update neural parameters of said first neural network and said second neural network independently, to improve generation of features by said first neural network and by said second neural network that improve prediction success of said comparison neural network.

The first trained neural network is deployed. Wearable sensor data from a monitored human subject is captured.

The captured wearable sensor data is sent to the first trained neural network, and the first trained neural network generates a set of features responsive to a time-window of the captured wearable sensor data. The trained classifier maps the generated features to one or more classes of activity in the time-window.

Based on said classification, one or more actions are performed. In one example, the action is quantifying health effects between at least a control group receiving a first intervention or no intervention and a test group receiving a second intervention in a clinical trial. In another example, the action includes determining possible health changes in the monitored human subject. In yet other examples, the action is issuing an alert to a clinician to investigate the health of the monitored human subject.

In yet another example, the action includes selectively controlling the actuation or deactivation of a device. In other examples, the action is controlling the operation or setting a parameter of a medical device associated with treating or monitoring the monitored human subject. In still another example, the action is controlling the operation or setting a parameter of a user electronic device associated with treating or monitoring the monitored human subject.

In yet others of these embodiments, wearable sensor data is captured from a monitored human subject. A first neural network generates a set of features responsive to a time-window of the wearable sensor data. A trained classifier mapping the generated features to one or more classes of activity in said time-window. Based on said classification, one or more actions are performed. In one example, the action is quantifying health effects between at least a control group receiving a first intervention or no intervention and a test group receiving a second intervention in a clinical trial. In another example, the action includes determining possible health changes in the monitored human subject. In yet other examples, the action is issuing an alert to a clinician to investigate the health of the monitored human subject.

In yet another example, the action includes selectively controlling the actuation or deactivation of a device. In other examples, the action is controlling the operation or setting a parameter of a medical device associated with treating or monitoring the monitored human subject. In still another example, the action is controlling the operation or setting a parameter of a user electronic device associated with treating or monitoring the monitored human subject.

The first neural network is created by: obtaining a first collection of samples of wearable sensor data from a plurality of humans with a first type of wearable sensor; obtaining a second collection of samples of wearable sensor data from a plurality of humans with a second type of wearable sensor, at least some of said samples being matched to the same human and substantially the same time-window as samples of the first collection; training the first neural network by iteratively: inputting samples from the first collection to the first neural network to generate features; inputting samples from the second collection to a second neural network to generate features; inputting features from the first neural network together with features from the second neural network to a comparison network that predicts whether input samples were matched or mis-matched; back propagating to the first neural network and the second neural network an error generated by a cost function that penalizes failure to correctly determine whether the input samples are matched or mis-matched, to update neural parameters of the first neural network and the second neural network independently, to improve generation of features by the first neural network and by the second neural network that improve prediction success of the comparison neural network.

Referring now to FIG. 1A, one example of a system 100 that trains neural networks comprises a first neural network 102, a second neural network 104, a comparison neural network 106 (coupled to the first neural network 102 and the second neural network 104), and a control circuit 108 (coupled to the first neural network 102, the second neural network 104, and the comparison neural network 106). As shown in FIG. 1A, these elements are used in a training phase according to the approaches described herein.

The first neural network 102, the second neural network 104, and the comparison neural network 106 may be any kind of neural network or deep neural network such as a convolutional neural network (CNN). Other examples of neural networks are possible. The first neural network 102 is configured to receive a first set of wearable sensor data and responsively produce a first feature vector 107. The first wearable sensor data describes first physiological features of one or more training humans 112. Any labels in the first set of wearable sensor data are ignored by the first neural network 102. By "labels," it is meant any identifier that would serve to identify the source, content, or other features of the data. The training humans 112 have wearable sensors 114 and 115. The wearable sensors 114 and 115 may be any type of sensors such as chest sensors or wrist sensors. These sensors may obtain readings of waveform data such as accelerometers or gyroscopes that characterize movement as experienced at the location the sensor is worn. These sensors may also obtain readings of waveform data such as electrocardiographic signals, impedance signals, photoplethysmographic signals, among others. These sensors may further record data such as skin and ambient temperatures, and may compute in sensor firmware derived vital sign features such as heartbeat or breathing rates. A wristwatch sensor and an adhesive torso patch sensor are known in the art to collect the aforementioned data, to mention two examples. The neural networks 102, 104, and 106 may be formed and stored in a database or other electronic memory device. The database 116 is any type of electronic memory device that stores information electronically.

The second neural network 104 is configured to receive a second set of second wearable sensor data. The second neural network 104 responsively produces a second feature vector 109. The second wearable sensor data describes second physiological features of the human 112 as described above. Any labels in the second set of wearable sensor data are ignored by the second neural network 104. As before, by "labels" it is meant any identifier that would serve to identify the source, content and/or other features of the data. For purposes of human activity recognition, a preferred embodiment uses a wristwatch style sensor with at least a continuous 3-axis accelerometer sampled at 5 Hz or more and an adhesive torso patch with at least a continuous 3-axis accelerometer sampled at 5 Hz or more. The first feature vector 107 and second feature vector 109 represent features in the input signal that are characteristic of, for example, running, standing, exercising, walking at a particular speed, climbing stairs, riding a bike, driving a car, playing a particular game, or engaging in a particular activity to mention a few examples.

In aspects, the first feature vector 107 and second feature vector 109 are groupings of node output values, which have numeric values (e.g., real numbers or integers). These values are generated by means of an activation function of the neural network 102 or 104 that represents the level of activation of the nodes at the output layer of the neural network 102 or 104. Activation functions may take the form of functions such as sigmoid, arctan, hyperbolic tangent, rectified linear unit (ReLU), leaky ReLU, exponential linear unit (ELU), and the like, which are known in the art. The number of such nodes in any neural network (and thus the length of the vector) may be in the order of tens or hundreds of nodes. Each such node receives inputs from other nodes at higher or upstream layers of the neural network, which represent the activation values of those nodes. The inbound activation values are multiplied by learned weights to yield numbers that are summed at each node. In this way, the inbound activation value from any given upstream node may be amplified or attenuated by the weight on that connection, as it contributes to the overall sum of inbound activations to the node. Added to that sum for each node is a bias value as well. Learned weights and biases are updated when the neural network is trained by backpropagation of error as described elsewhere herein. Adjustment of these weights and biases improves performance of the neural networks 102 and 104 based on the task by which error is measured.

The control circuit 108 may train and apply inputs to the neural networks 102, 104, and 106 and cause the neural networks 102, 104, and 106 to produce outputs (e.g., the vectors described herein). It will be appreciated that as used herein the term "control circuit" refers broadly to any microcontroller, computer, or processor-based device with processor, memory, and programmable input/output peripherals, which is generally designed to govern the operation of other components and devices. It is further understood to include common accompanying accessory devices, including memory, transceivers for communication with other components and devices, etc. These architectural options are well known and understood in the art and require no further description here. The control circuit 108 may be configured (for example, by using corresponding programming stored in a memory as will be well understood by those skilled in the art) to carry out one or more of the steps, actions, and/or functions described herein.

At least some of the first set of wearable sensor data and the second set wearable sensor data are obtained from the same human activity of the same human 112 occurring at the same time. By "time," it is meant a time period, time window, time frame, or an instant in time (e.g., a specific time value).

The comparison neural network 106 is configured to predict whether the first feature vector 107 from the first neural network 102 and the second feature vector 109 from the second neural network 104 are matched or mis-matched. The first feature vector 107 and second feature vector 109 are determined to be matched when the first feature vector 107 and the second feature vector 109 are derived from input data from the same human and taken at substantially the same time. This determination may be made from the timestamps of the collected data and knowledge of which human subjects the wearable sensor data came from, and avoids the dilemma of post-hoc hand-labelling with an activity classification by human expert. Sets of matched and mismatched data can easily be generated by programmed data parsing in an automated way from a library of collected human subject wearable sensor data. The prediction by comparison neural network 106 may be made by comparing vectors that are output by the networks 102 and 104. In these regards, a cross entropy loss as to whether the prediction regarding matching is correct is determined. This value may be calculated by an error function and used to train the neural networks 102 and 104.

Generally speaking, training the neural networks 102 and 104 involves two distinct phases. The first phase is the forward pass through the neural network 102 or 104, where the network parameters are frozen, an input is provided to the network 102 or 104, and the network 102 or 104 produces an estimate of the target output value. It will be appreciated that the training alters the physical characteristics of the neural networks and classifiers described herein.

The second phase, known as the backward pass through the neural network 102 or 104, involves the control circuit 108 calculating the amount of error as to whether the vectors 107 and 109 have been correctly determined to be matched or mis-matched. In examples, a partial derivative of each network parameter with respect to the error is calculated by a cost function for each layer in the network 102 or 104. The neural network parameters of the networks 102 and 104 are then updated by subtracting a small multiple of each respective parameter's partial derivative. The cost function penalizes a failure to correctly determine whether the vectors are matched or mis-matched. This back propagating process is effective to independently update parameters of the neural networks to produce a first trained neural network 102 and a second trained neural network 104.

Training is conducted across available batches of training data comprising matched or mismatched windows of data. The process is then repeated until the network 102 or 104 has learned to accurately produce estimates of the target output. Approaches for determining exactly when training is complete are known in the art and are applicable hereto, and typically involve achieving a desired level of performance by the comparison network 106, or when performance hits a maximal plateau.

Once this training step is completed, the trained neural networks 102 or 104 can be used to train a classifier 120. In other words, the deep learning models that produce the features are trained as discussed above. Once this training is complete, the trained network 102 and 104 are frozen and used to generate features for new input data that is labeled, and these features and labels are used to train the classifier 120.

In one specific example where a classifier can be trained to recognize walking behavior in contrast to all other activities, after the neural networks 102 and 104 are trained to analyze 1-second windows of data, a small amount of labelled walking data is used to build a classifier using the features from the networks 102 and 104 by inputting a 1-second window of accelerometer data to one or the other of networks 102 and 104 corresponding to the type of sensor from which the accelerometer data comes, where that accelerometer data is known to be captured during walking or known to be captured during an activity that is not walking, and generating the resulting feature vector for each such sample. These feature vectors are then used with a traditional random forest classifier to classify every one second of accelerometer data as "walking" or "not walking".

The classifier 120 used herein may be any number of different types, including a random forest, neural network, logistic regression, support vector machine, etc. Once trained, the classifier 120 is used to estimate an activity label from features (e.g., in the form of vectors) applied to the classifier 120. The activity label denotes the type of activity detected and this can be used as discussed herein to perform various actions.

Figure 1B:
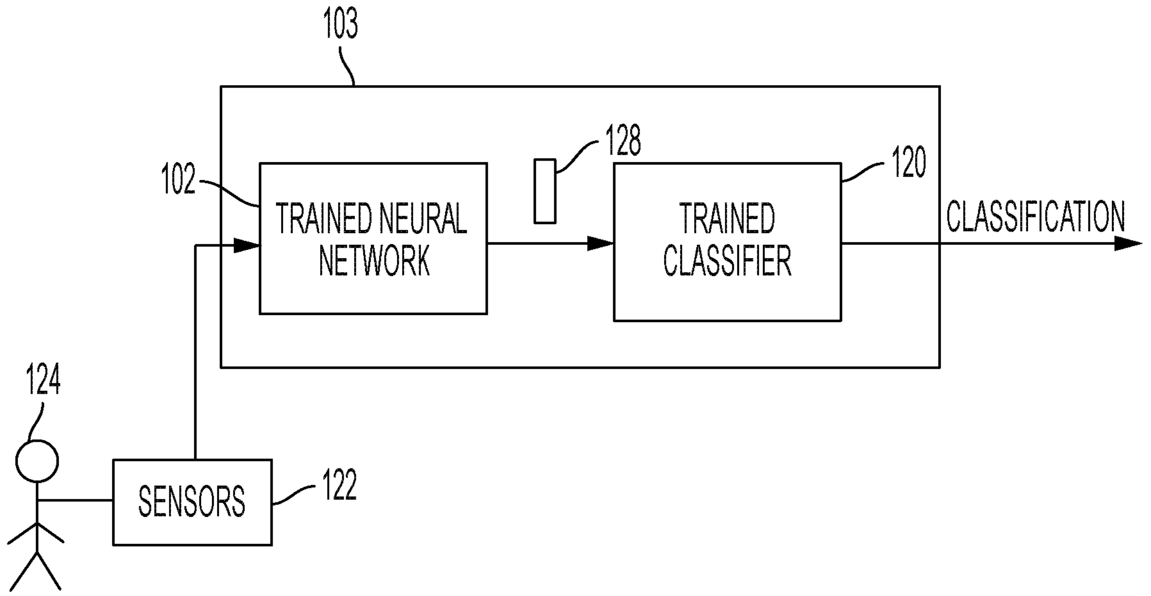
FIG. 1B comprises a diagram of a system as configured in accordance with various embodiments of these teachings.

Referring now to FIG. 1B, one example of using trained neural networks and a trained classifier (e.g., obtained from the approach of FIG. 1A) in a monitoring phase is described. In one example, the process of FIG. 1A (or a similar process) has been executed to produce trained neural networks 102 and 104 and the trained classifier 120. Either of these trained networks 102 and 104 are deployed and have data applied to responsively produce feature vectors.

In the example of FIG. 1B, the trained first neural network 102 is deployed. In aspects, the system 100 further comprises the trained classifier 120 and wearable sensors 122. The wearable sensors 122 are worn by a current human subject 124. In examples, the wearable sensors 122 can be chest or wrist sensors to match the deployed network. Other examples of sensors are possible. It will be appreciated that the second trained neural network 104 may also be deployed and the following description would also be applicable.

In aspects, the trained neural network 102 and the trained classifier 120 may be deployed at a central location 103. The central location 103 may be a business, headquarters, home office, data center or other physical location. In another example, the trained neural network 102 may be deployed at a remote location, for example, at a hospital, doctors office, or research facility. Other examples are possible. Data from sensors may be uploaded to location 103 by mobile digital communication network or by local area network or other means. Uploads can occur periodically or continuously.

The first trained neural network 102 is deployed and current wearable sensor data is obtained from the current human subject 124 by the wearable sensors 122 and applied to the first trained neural network 102 to obtain a current feature vector 128. At the trained classifier 120, the current feature vector 128 is applied to the trained classifier 120 where it is mapped to a classification representing one or more classes of activity. In aspects, the mapping utilizes known and labeled vectors from other monitored human subjects. In other aspects, the mapping comprises comparing the current feature vector 128 to known and labeled vectors from other monitored human subjects and determining the activity class by a nearest neighbor calculation.

Based on the classification one or more actions are performed. In one example, the action is quantifying health effects between at least a control group receiving a first intervention or no intervention and a test group receiving a second intervention in a clinical trial. In another example, the action includes determining possible health changes in the monitored human subject 124. In yet other examples, the action is issuing an alert to a clinician to investigate the health of the monitored human subject 124.

In still another example, the action includes selectively controlling the actuation or deactivation of a device. In other examples, the action is controlling the operation or setting a parameter of a medical device associated with treating or monitoring the monitored human subject 124. In still another example, the action is controlling the operation or setting a parameter of a user electronic device associated with treating or monitoring the monitored human subject 124. For example, the frequency, speed, and/or scope of the treatment or the monitoring may be changed. Settings on these devices (e.g., involving video or display quality or characteristics involving font sizes, colors, or other characteristics on screens of these devices) may also be controlled and changed, for example, in the displaying of alerts (e.g., based upon the type of alert).

Figure 2:
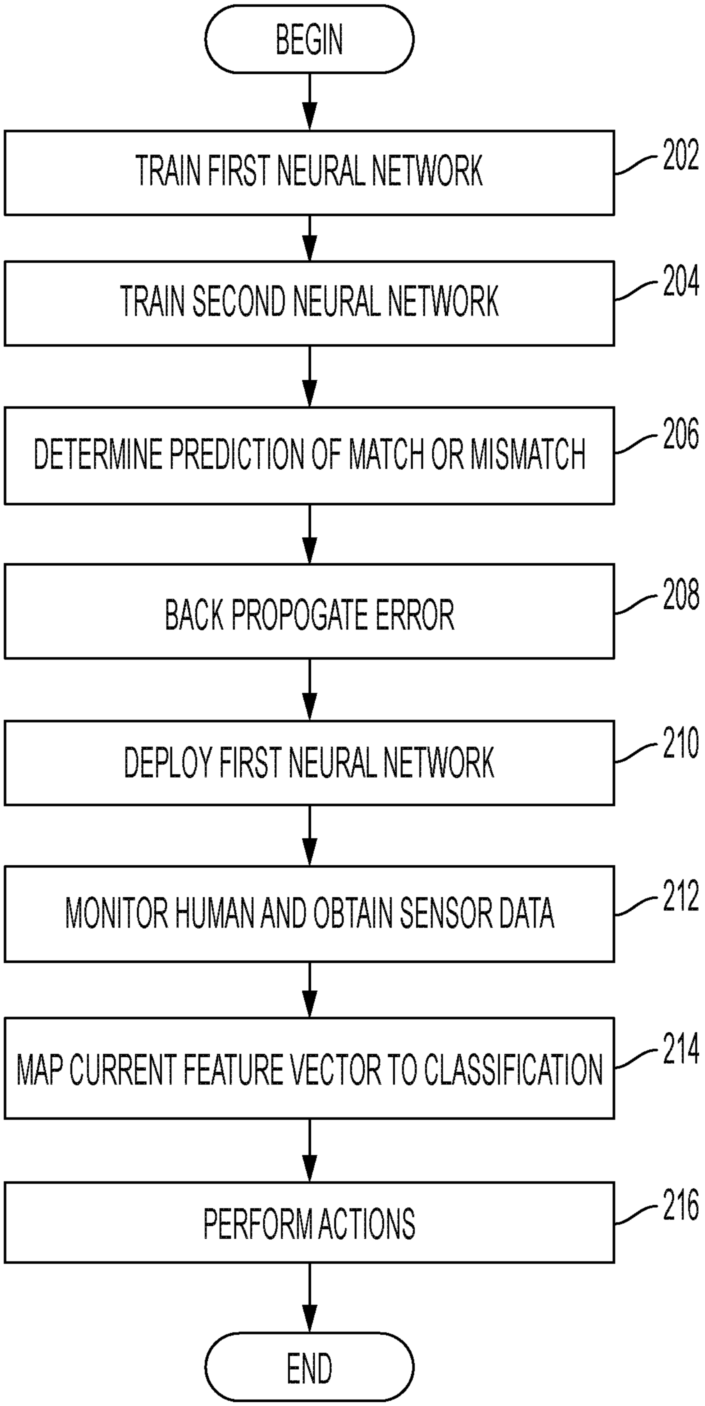
FIG. 2 comprises a flowchart of an approach in accordance with various embodiments of these teachings.

Referring now to FIG. 2, an approach for training and utilizing a trained neural network is described.

At step 202, a first neural network is iteratively trained to obtain a first trained neural network and at step 204 a second neural network is iteratively trained to obtain a second trained neural network. The training includes receiving a first set of wearable sensor data at the first neural network. The first neural network responsively produces a first feature vector, and the first wearable sensor data describes first physiological features of a human. Any labels in the first set of wearable sensor data are ignored. In aspects, the sensors are wrist sensors or chest sensors.

The training further includes receiving a second set of second wearable sensor data at the second neural network. The second neural network responsively produces a second feature vector. The second wearable sensor data describes second physiological features of the human. Any labels in the second set of wearable sensor data are ignored. At least some of the first set of wearable sensor data and the second set of wearable sensor data are obtained from the same human activity of the same human occurring at the same time.

At step 206 and at a comparison neural network a prediction is made as to whether the first feature vector from the first neural network and the second feature vector from the second neural network are matched or mis-matched. The first feature vector and second feature vector are determined to be matched when the first feature vector and the second feature vector are determined to be from the same human and taken at substantially the same time or time period. In aspects, the comparison network comprises an ensemble of separate comparison networks with different time scales of a fixed input window size.

At step 208, an error is back propagated to the first neural network and the second neural network where the error is generated by a cost function that penalizes a failure to correctly determine whether the vectors are matched or mis-matched. The backpropagation and application of the error to the neural networks is effective to independently update parameters of the first neural network and the second neural network to optimize a generation of features by the first neural network and the second neural network and to optimize prediction success of the comparison neural network.

In examples, the first neural network, second neural network are trained using steps 202, 204, and 206 at a central location. These elements can also be deployed at separate and different locations.

At step 210, the first trained neural network is deployed. For example, the first neural network may be deployed at a central location so that it can conveniently be used to receive data.

At step 212, at least one current human subject is monitored to obtain current wearable sensor data and the current wearable sensor data is applied to the first trained neural network to obtain a current feature vector.

At step 214 and at a trained classifier, the current feature vector is mapped to a classification representing one or more classes of activity. The classifier itself may be trained. In examples, the mapping utilizes known and labeled vectors from other monitored human subjects, and outputs the class of the nearest neighbor or centroid of neighbors to the current feature vector using a k-nearest neighbor approach. In aspects, the trained classifier comprises a random forest or a third neural network. Other examples are possible.

At step 216 and based upon the classification, one or more actions are performed. The actions can take a variety of different forms.

In one example, the action is quantifying health effects between at least a control group receiving a first intervention or no intervention and a test group receiving a second intervention in a clinical trial. In another example, the action includes determining possible health changes in the monitored human subject. In yet other examples, the action is issuing an alert to a clinician to investigate the health of the monitored human subject.

In yet another example, the action includes selectively controlling the actuation or deactivation of a device. In other examples, the action is controlling the operation or setting a parameter of a medical device associated with treating or monitoring the monitored human subject. In still another example, the action is controlling the operation or setting a parameter of a user electronic device associated with treating or monitoring the monitored human subject. In examples, the user electronic device is a smartphone, a personal computer, a laptop, or a tablet. Other examples of sensors and user electronic devices are possible.

Figure 3:
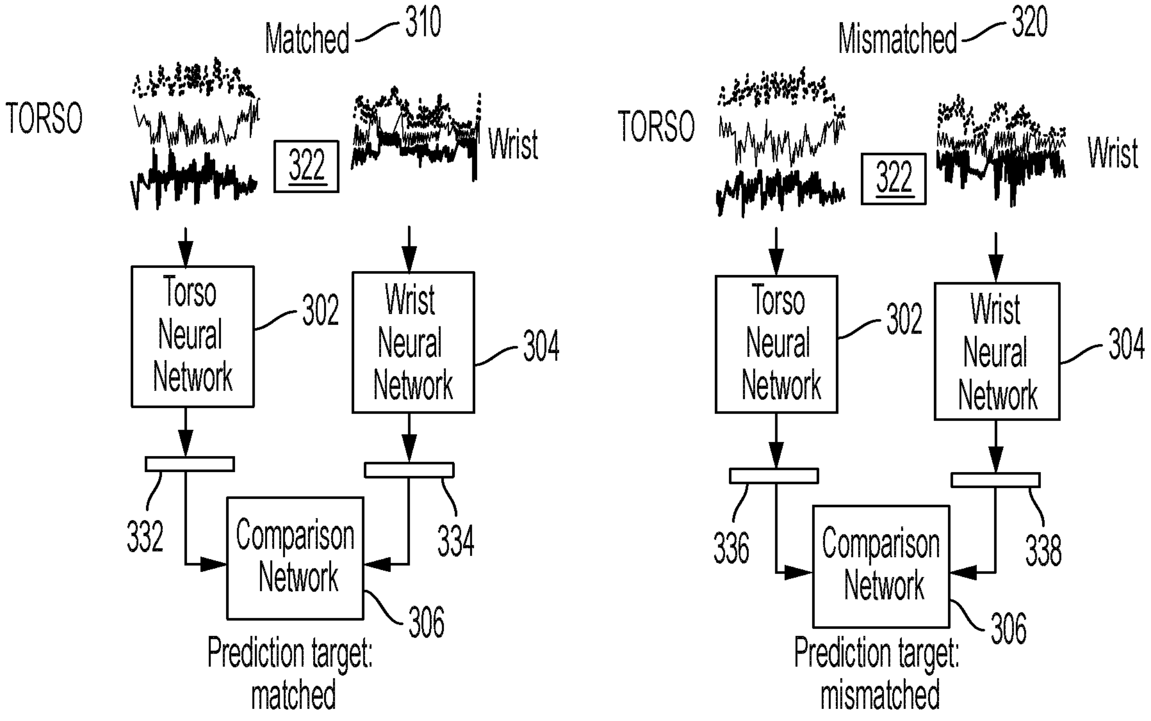
FIG. 3 comprises a diagram of a system as configured in accordance with various embodiments of these teachings.

Referring now to FIG. 3, one example of an approach for training neural networks is described. In this example, a torso neural network 302 models activity of humans measured by sensors on a human torso (e.g., chest sensors such as chest patches), and a wrist neural network 304 that models activity of humans measured by wrist sensors. A comparison neural network 306 is also provided. It will be appreciated that these are two examples of sensors and locations for sensors on humans and that other types of sensors and/or locations on humans are possible.

The example shows that matched accelerometer data 310 and mis-matched paired accelerometer data 320 are used to train the neural networks 302 and 304. The torso accelerometer data remains the same between both the matched data 310 and the unmatched data 320, but the wrist accelerometer data is changed to a selected segment of wrist accelerometer signals that are from a different time point or time period as when the torso accelerometer segment was collected.

At step 322, the accelerometer data from pairs of matched and mis-matched time periods are provided to one of two networks, the torso neural network 302, and the wrist neural network 304, depending on the source of the data. In one example, the torso neural network 302 and wrist neural network 304 are multi-layered convolutional neural networks, each producing a single vector representation of the input accelerometer segment. More specifically, the torso neural network 302 produces a vector 332 (a single vector representation of the chest or torso input accelerometer segment) and the wrist network produces a vector 334 (a single vector representation of the wrist input accelerometer segment). With the mis-matched data 320, the torso neural network 302 produces a vector 336 (a single vector representation of the torso input accelerometer segment) while the wrist neural network 304 produces a vector 338 (a single vector representation of the wrist input accelerometer segment that is selected from a different point in time as to when the torso data was collected).

The vectors 332 and 334 of paired accelerometer segments generally look like each other (e.g., they may be the same or have slight deviations in amplitude, pattern, shape, size, or other characteristics), while the vectors 336 and 338 of mis-matched segments look much less like each other (e.g., they are different and/or have greater deviations in amplitude, pattern, shape, size, or other characteristics). The comparison network 306 takes in the vector representations of the activity and tries to correctly decide if the vectors represent matched data or mis-matched data. An error signal from the comparison network is then generated. The error signal represents whether a correct or incorrect determination as to whether the data is match/mis-matched has been reached. The error signal is then back-propagated to the networks 302 and 304, forcing the torso neural network 302 and wrist neural network 304 to learn increasingly nuanced descriptions of the accelerometer data, so that the comparison network 306 can correctly classify them.

To take one specific example, the matched data 310 is from a time period while the subject was walking, but the mis-matched data 320 is from a different time period of walking. To differentiate the two activities, it is not enough that the torso neural network 302 and wrist neural network 304 learn that the data represents walking. The torso neural network 302 and the wrist neural network 304 must provide even more sub-classifications to differentiate or classify the data, e.g., further classify the walking by characteristics like walking-speed and/or gait style to mention two examples. In this manner, the networks 302 and 304 can learn rich descriptions of the underlying activity, without needing to know the exact activity or the exact nature of the activity.

It can be seen that the present approaches simultaneously collect data from two or more locations on the body at the same time and indicate that the paired data is from the same person and activity. Artificial data is introduced and distinguishes from the activity determined because it is known the mis-matched data cannot be from the same activity. These approaches avoid the use of labels and the need to assign labels to data during this training process for deep neural networks because simultaneously collected data from the same person must be from the same activity class, whatever that class may be.

Once the torso neural network 302 and the wrist neural network 304 have been trained in this manner, they may be used in various ways. For example, the learned features may be used with a small amount of hand labelled activity data, and a conventional classifier may be trained to convert the features to a desired set of activity classifications.

The torso neural network 302 and wrist neural network 304 may be fine-tuned with a small hand labelled set of activity data for a desired set of activity classifications.

As described elsewhere herein, the trained torso or wrist neural networks can be deployed in a monitoring phase, monitored human data applied to the trained neural networks, and the resultant vectors from the trained neural networks applied to a trained classifier. To train the classifier, vectors produced by the torso neural network 302 and the wrist neural network 304 may also be applied to a "one-shot" classifier on-the-fly.

For example, a clinician has a human subject in physical therapy perform a type of therapy while wearing a wearable device. The features from that therapy could be used to train a classifier for that specific action as performed by that subject. The clinician could then quantify how well the subject complied with their physical therapy regime, thereby training the classifier to associate vectors with "good" or "bad" compliance.

In another specific example, a clinician can demonstrate correct and incorrect ways to do a certain activity during physical therapy, training a one-shot classifier or distance metric to recognize "good" vs "bad" (or degrees therein) of the activity. Later on, when the human subject performs the activity on their own at home, sensor signals are applied to the trained neural network, the output vectors of the trained neural network applied to a classifier, and the classifier can classify the activity as being performed correctly or incorrectly. A device could alert the human subject if they are performing the activity incorrectly.

In still other examples, sensor data is applied to a trained neural network producing vectors that represent attributes of features that show the effect of a drug (assuming that the features capture these attributes). For example, detection of a gait style may indicate certain effects of a drug taken by the human subject.

Figure 4:
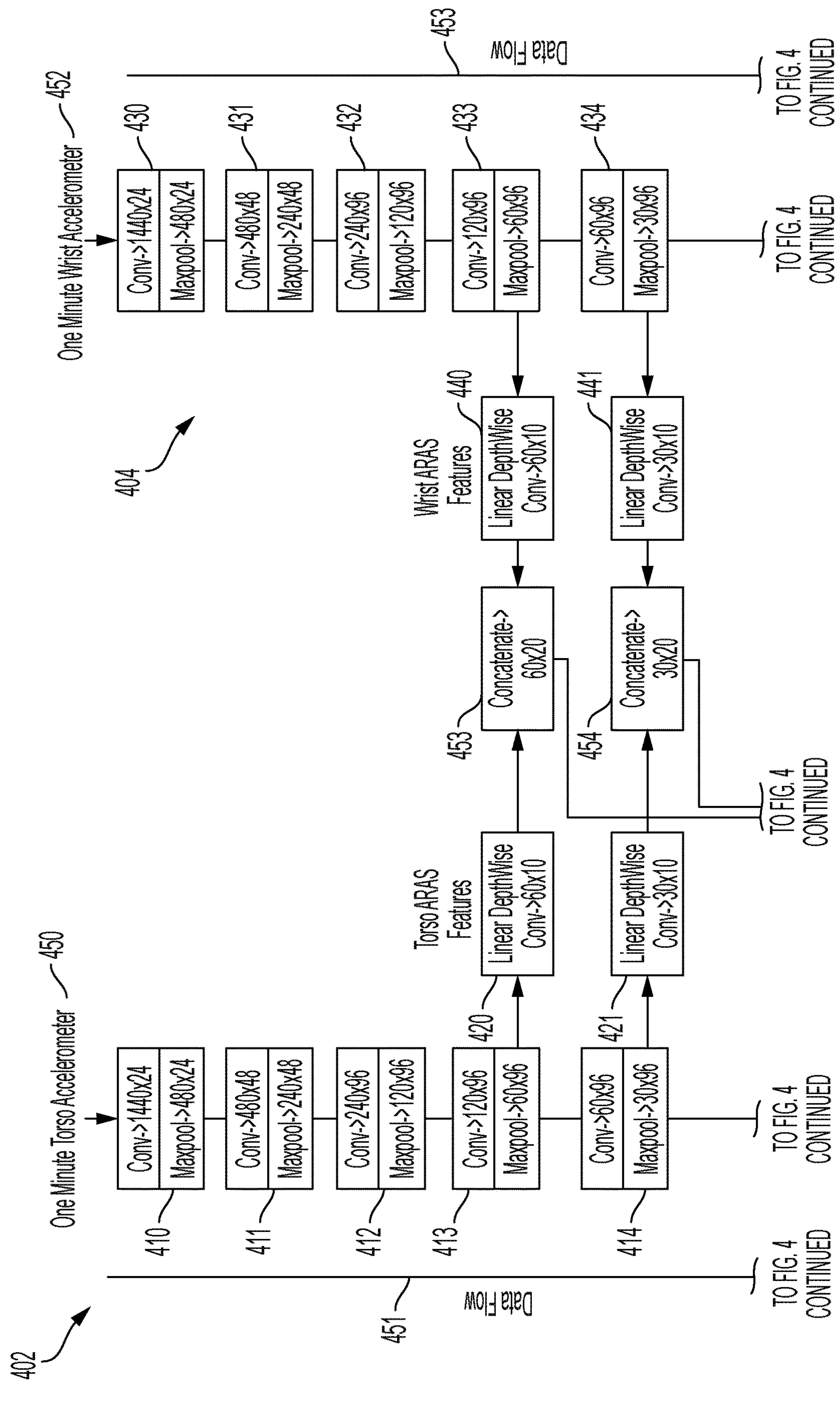
FIG. 4 comprises a diagram of a system as configured in accordance with various embodiments of these teachings.
Figure 4:
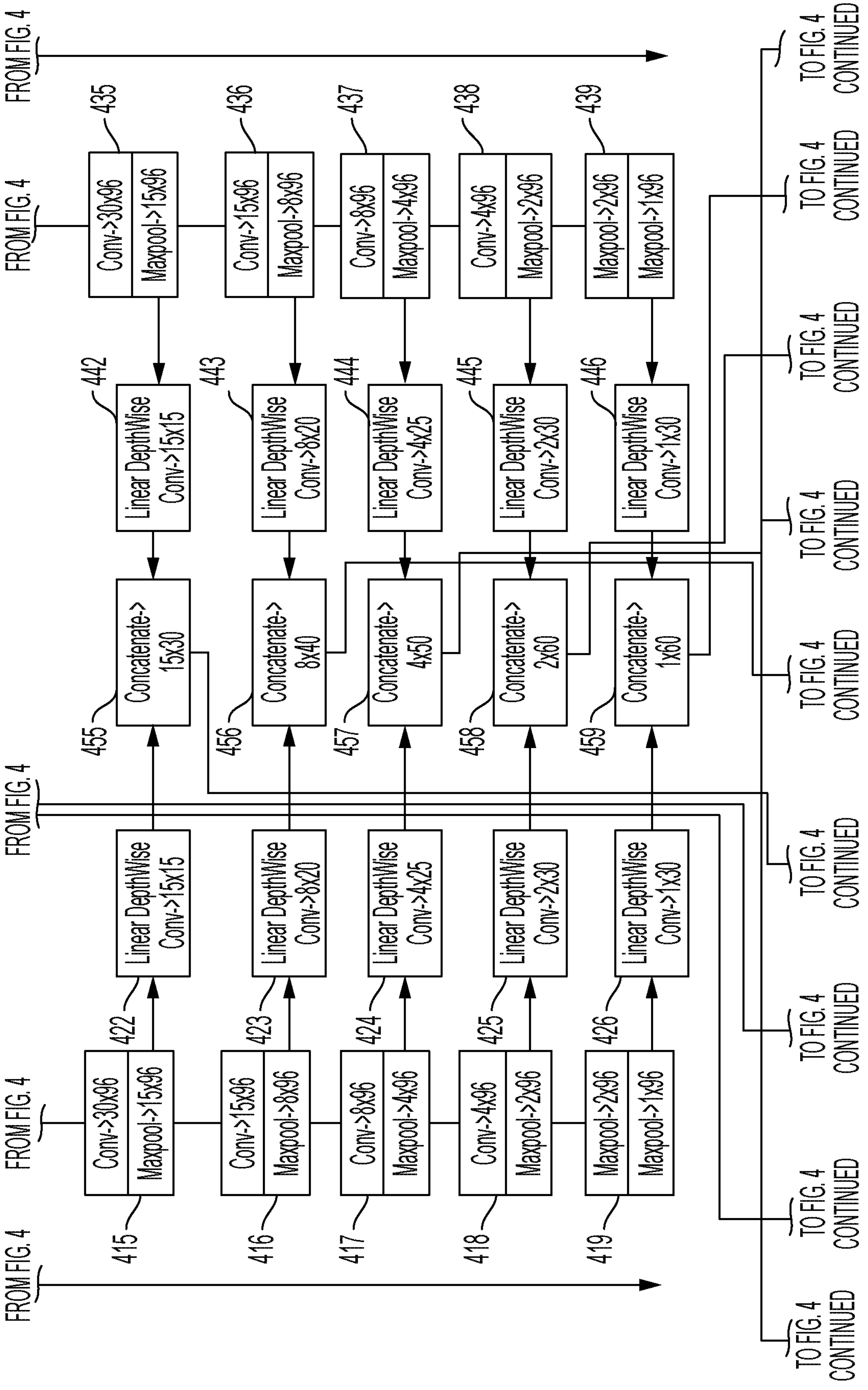
Figure 4:
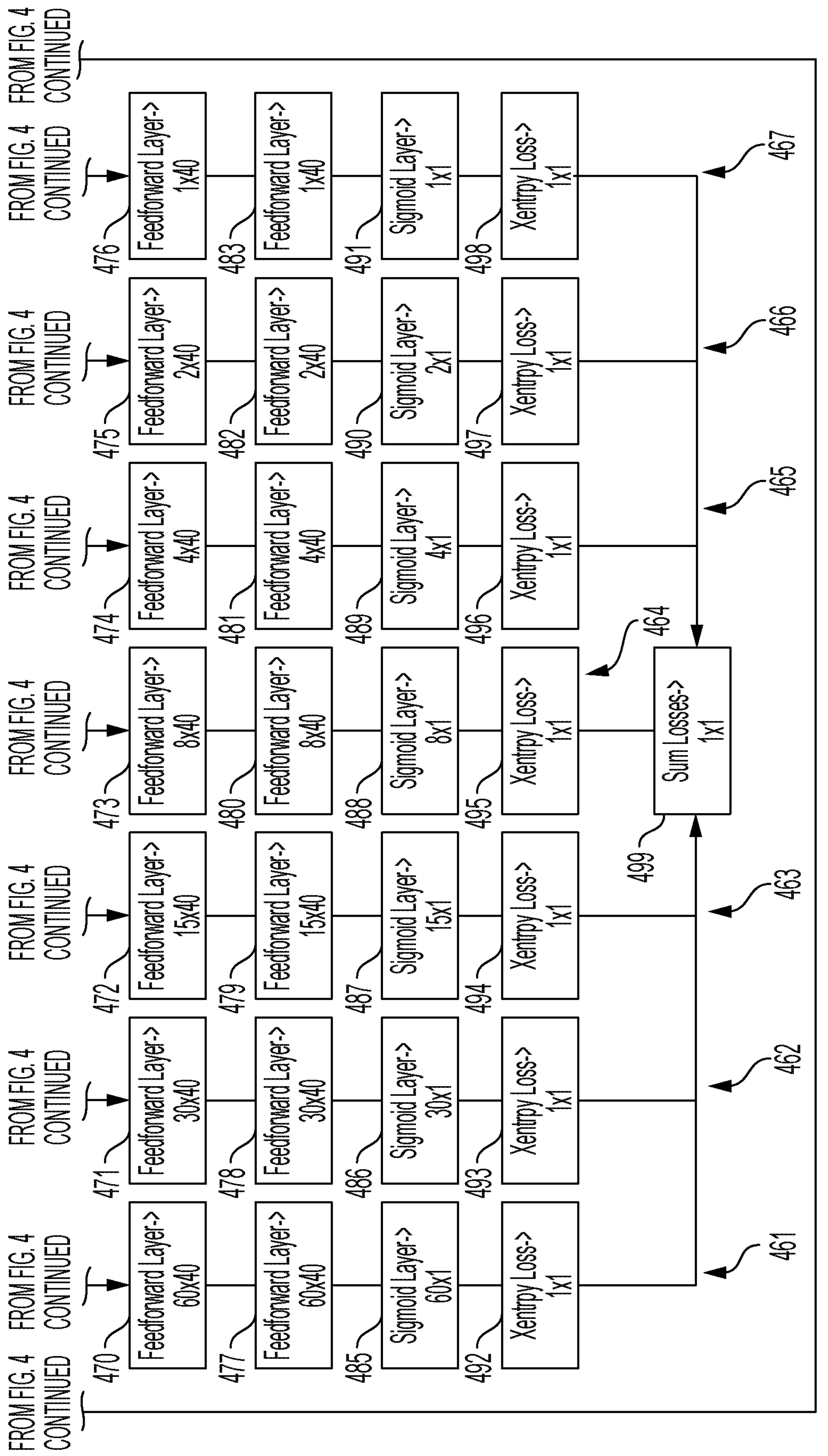

Referring now to FIG. 4, an example showing an apparatus for training neural networks is described. In this example, accelerometer inputs are used as inputs to neural networks. In addition, additional signal inputs (e.g., gyroscopes) may be used. Although two neural networks are trained in this example, it will be appreciated that more than two neural networks can be used.

As described herein, these approaches provide for the comparison between two time windows of accelerometer data taken from different devices. In aspects, a multi-window time scale vector is created. Producing multiple vectors of differing time scales allows each vector to capture features related to its time scale, in aspects, from 1 second level features, up to 1 minute level features. The features are meant to be general purpose activity recognition features, and as such it is not known beforehand what time scale will be best for every activity recognition task. As an example, a feature vector created from a 4 second window would likely be appropriate for making running or walking detection but would be insufficient for determining higher level activities such as "playing basketball". In one alternative embodiment, if the desired feature window size was known before training the features, then using multiple window timescales would not be necessary, and only the desired feature window size would be needed.

In other examples, a convolutional network utilizing dilated convolutions can keep the same input and output at each network layer, but the network receptive field (how much time the network is "looking at" at a given network depth) doubles at each layer. In such a network, the outputs from each layer could be similarly paired.

Turning now to FIG. 4, a torso neural network 402 includes various blocks that perform convolutional and maxpool operations. Convolution and maxpool operations roughly halve the time resolution of data received at each of these blocks. In this way, the features produced at each layer become more and more general and high level, and less specific. The blocks performing these functions include blocks 410, 411, 412, 413, 414, 415, 416, 417, 418, and 419.

Linear depth wise convolutional layers 420, 421, 422, 423, 424, 425, and 426 shrink the number of features (dimensions) of the data. In aspects, the linear depth wise convolution simply perform a weighted average along the feature dimension to produce (in one example) a 60×10 output feature vector. Linear depth wise convolutional layers 420, 421, 422, 423, 424, 425, and 426 are linear layers because the learning occurs in the main path of the neural network producing a dimensionality reduction of the information.

A wrist neural network 404 includes various blocks that perform convolutional and maxpool operations. The blocks performing these functions include blocks 430, 431, 432, 433, 434, 435, 436, 437, 438, and 439. Convolution and maxpool operations roughly halve the time resolution at each of these blocks. In this way, the features produced at each layer become more and more general and high level, and less specific. Linear depth wise convolutional layers 440, 441, 442, 443, 444, 445, and 446 shrink the number of features (dimensions). The linear depth wise convolution performs a weighted average along the feature dimension to produce in one example a 60×10 output feature vector. As before, linear depth wise convolutional layers 440, 441, 442, 443, 444, 445, and 446 are linear layers because the learning happens in the main path of the neural network producing a dimensionality reduction of the information.

Data 450 flows through the torso neural network 402 in the direction indicated by the arrow labeled 451. Data 452 flows through the wrist neural network 404 in the direction indicated by the arrow labeled 453.

Generally, the data 450 flows through the network 402 and data 452 flows through the network 404. The data is reduced in size by each block of the respective neural networks. As mentioned, some blocks flow to the linear depth wise convolutional layers.

The linear depth wise convolutional layers from each of the torso neural network and the wrist neural network are combined at concatenators 453, 454, 455, 456, 457, 458, and 459. The output of the concatenators 453, 454, 455, 456, 457, 458, and 459 flows to a comparison neural network 460, which includes seven neural networks 461, 462, 463, 464, 465, 466, and 467. The chest and wrist features are concatenated together, as shown. Once the features are combined, the 7 resolutions of features (from once per second to once per minute) are input into the 7 separate feedforward comparison neural networks 461, 462, 463, 464, 465, 466, and 467 that form an overall comparison neural network 460.

The seven comparison neural network include feedforward layers 470, 471, 472, 473, 474, 476, 477, 478, 479, 480, 481, 428, and 483, and sigmoid layers 485, 486, 487, 488, 489, 490, and 491, and cross-entropy (aka, "x-entropy") layers 492, 493, 494, 495, 496, 497, and 498. The outputs of data passing through each of these are summed at step 499 into a single loss. For example, data from concatenator 453 goes to feedforward layer 470, feedforward layer 477, sigmoid layer 485, and x-entropy layer 492 to produce a loss over network 461, which is summed from the losses of the other networks 462, 463, 464, 465, 466, and 467 to produce the overall loss 499.

The sigmoid activation blocks 485, 486, 487, 488, 489, 490, and 491, produce a "match" or "mis-matched" probability for each timestamp in the feature vector (e.g., a 60×1 probability for the once per second features input to network 461, and a 2×1 probability for the once every 30 second features input to network 466).

The networks 402 and 404 are then trained to minimize the sum of the total cross entropy loss across all time resolutions at step 499. This is back-propagated to the torso neural network 402 and the wrist neural network 404 to train these networks. Weights are adjusted within these networks, in one example.

In one example of the operation of this system of FIG. 4, data sample 450 from torso sensors comprises a 60-second window of 3-axis accelerometry waveform data. Similarly, data sample 452 from wrist sensors also comprises a 60-second window of 3-axis accelerometer waveform data. The 3-axis accelerometer measures vibration or movement in each of the 3 orthogonal directions conventionally known as x, y and z, with respect to the plane of the circuit board of the sensor device (wrist or chest patch) on which the accelerometer is mounted. Human walking movement thus is expressed in a complex fashion from either the wrist location or the chest location, or other location as to which a sensor might be applied, in the orthogonal directions of the accelerometer unit, but inherently encode for relevant movements such as heel strike, swing and sway of typical human walking behavior. Non-walking behavior will be expressed in some other complex fashion from such locations in the orthogonal directions of the accelerometer unit, and will inherently be encoded.

The accelerometer data for each window is resampled to 24 hz (hertz, samples per second), so that the input data has 1440 samples in the time dimension, and 3 accelerometer channels (e.g., a 1440×3 input). Initially, 4 convolutional and maxpooling layers are applied to the resampled accelerometer signal data, building up features in the channel dimension, and down sampling to lose time resolution.

The wrist data 403 is applied to block 430 (producing a 1440 by 24 output of the convolutional layer, then a 480 by 24 output of maxpool) then block 431 (producing a 480 by 48 output of the convolutional layer, then a 240 by 48 output of maxpool), then block 432 (producing a 240 by 96 output of the convolutional layer, then a 120 by 96 output of maxpool), then block 433 (producing a 120 by 96 output of the convolutional layer, then a 60 by 96 output of maxpool), then block 434 (producing a 60 by 96 output of the convolutional layer, then a 30 by 96 output of maxpool), then block 435 (producing a 30 by 96 output of the convolutional layer, then a 15 by 96 output of maxpool), then block 436 (producing a 15 by 96 output of the convolutional layer, then a 8 by 96 output of maxpool), then block 437 (producing a 8 by 96 output of the convolutional layer, then a 4 by 96 output of maxpool), then block 438 (producing a 4 by 96 output of the convolutional layer, then a 2 by 96 output of maxpool), and then block 439 (producing a 2 by 96 output of the convolutional layer, then a 1 by 96 output of max-pool).

At layer 433 (layer 4), the wrist input 1440×3 shaped data has been transformed to dimensions equal to 60×96; in other words, this is a 96-element vector for every second of data in the 60 second input. It is at this point where the first linear depth wise convolution filter 440 is applied to create the one second resolution level features. The linear depth wise convolution simply performs a weighted average along the feature dimension to produce a 60×10 output feature vector. It is a linear layer because the learning happens in the main path of the neural network; a linear layer is a dimensionality reduction of the information that already exists. Similar operations are performed by the other layers 441, 442, 443, 444, 445, and 446, from data siphoned from convolution/maxpool layers at 434, 435, 436, 437, 438 and 439. The same process is also applied to the torso data 401 through layers 410-419 and linear depth-wise layers 420-426.

Convolution and maxpool layers roughly halve the time resolution along each layer. In this way, the features produced at each layer become more and more "high level" or less specific or less general. However, using the linear depth-wise convolutions at each step allows for features along the entire hierarchy to be represented. It is these features which are used by the comparison network to determine matching/non-matching activities. At the highest level, there are 10 features for each of 60 seconds (60×10); at the lowest level there are 30 features for the whole minute (1×30).

The chest and wrist features are concatenated together by the concatenators 453, 454, 455, 456, 457, 458, and 459. Once the features are combined, the 7 resolutions of features (from once per second to once per minute) are input into 7 separate feedforward neural networks 461, 462, 463, 464, 465, 466, and 467. As mentioned, the feedforward networks 461, 462, 463, 464, 465, 466, and 467 have two feedforward (hidden) layers, a sigmoid layer with a sigmoid activation function, and a cross entropy layer producing a "match" or "mis-matched" probability for each timestamp in the feature vector (e.g., a 60×1 probability for the once per second resolution features in network 461, but a 2×1 probability for the once every 30 second resolution features in network 466). Cross entropy loss is averaged at each feed forward network, and averaged cross entropy losses are summed across all feed forward networks at 499.

The networks 402 and 404 are then trained to minimize the sum of the total cross entropy loss across all time resolutions using the value 499. This is back-propagated to the torso neural network 402 and the wrist neural network 404 to train these networks. By this backpropagation of error, both networks become better at producing features that are relevant to determining if the activity represented by the raw data from the sensors is matched or unmatched. Training is conducted across available batches of training data comprising matched or mismatched windows of data, until either a desired level of performance by the comparison network 460 is achieved in terms of error of prediction regarding matching, or performance hits a maximal plateau. Approaches for determining when training is complete are known in the art and are applicable hereto.

Separately and in other aspects, after the wrist neural network 404 and the torso neural network 402 are completely trained, a small amount of labelled data (e.g., labeled walking data) is used to build a classifier using the features from the torso and wrist convolutional networks 402 and 404 by up sampling every time resolution feature to once per second. For example, the feature values at layer 420 (which is 60×10) already have 60 sets of 10 values and no up-sampling is needed there. At feature values from layer 421 (30×10), each of the 30 sets of 10 values would be up-sampled by repeating the ten values once adjacent to each value. At feature values at layer 424 (4×25), each of the 4 sets of 25 values is repeated adjacently 14 more times to result in 4 groups of 15 sets of the 25 values. This is done for all time resolutions, thus producing a 140-dimension vector for every second of data, where the 140 values come from the 10, 10, 15, 20, 25, 30 and 30 feature values. These feature vectors are then used with a traditional random forest classifier to classify every one second of accelerometer data as "walking" or "not walking".

Figure 5:
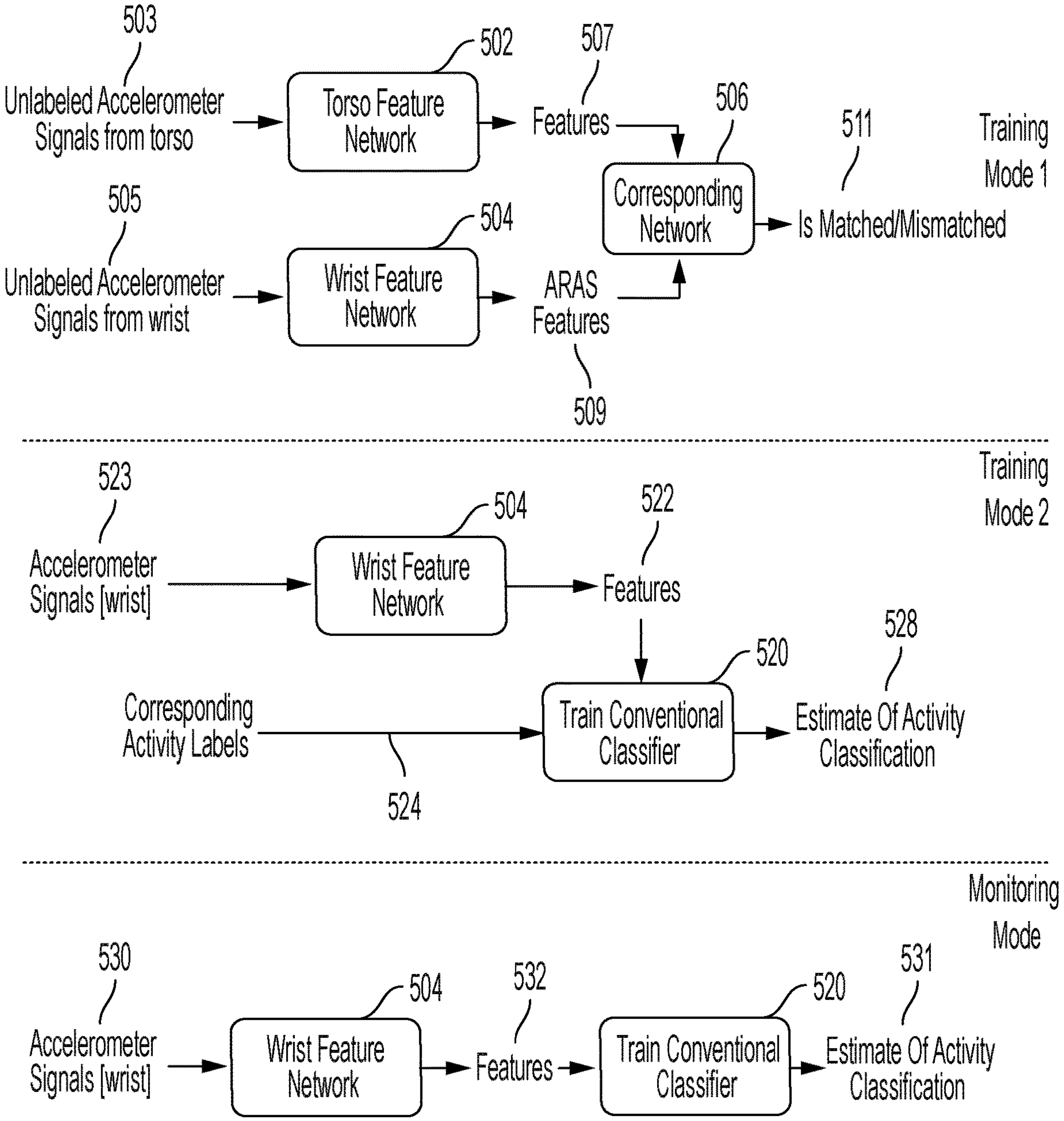
FIG. 5 comprises a diagram of a system as configured in accordance with various embodiments of these teachings.

Referring now to FIG. 5, another example of an approach of training and using neural networks is described. A torso feature neural network 502, a wrist feature neural network 504, and a comparison neural network 506 are utilized. The neural networks 502, 504, and 506 are neural networks as have been described elsewhere herein. The approach includes a first training mode, a second training mode, and a monitoring mode (that temporally follows the first training mode and the second training mode).

In the first training mode, unlabeled accelerometer signals 503 from a sensor deployed on the torso (e.g., the chest) of a human are applied to the torso feature neural network 502. Unlabeled accelerometer signals 505 from a sensor deployed on the wrist of a human (the same human and same time frame when "matched", but a different time frame and/or different human when "unmatched") are applied to the wrist feature neural network 504. The torso feature neural network 502 produces features 507 and the wrist feature neural network 504 produces feature vectors 509, which represent features or characteristics of the activity of the human(s) in respective time windows.

The feature vectors 507 and 509 are received at the comparison neural network 506. A cost function is used by the comparison neural network 506 to determine whether the vectors are matched or unmatched. The amount of matching or mis-matching is indicated by an error, which in examples is a numerical value. This value is applied to the neural networks 502 and 504, which, in examples, adjust parameters by subtracting a small multiple of each respective parameter's partial derivative. The cost function penalizes a failure to correctly determine whether the vectors are matched or mis-matched at step 511. This back propagation process is effective to independently update parameters of the neural network 502 and the neural network 504 and to produce a trained torso feature neural network 502 and a trained wrist feature neural network 504. Both networks become better at producing features that are relevant to determining if the activity measured by the sensors is matched or unmatched.

The neural networks 502 and 504 that produce the feature vectors 507 and 509 are trained in the first training mode. Once the first training mode is complete, the trained torso feature neural network 502 and/or the trained wrist feature neural network 504 are used to generate feature vectors in the second training mode. In this example of the second training mode, the trained wrist feature network is used to produce feature vectors 522 from this trained network and these are used as the input to a classifier 520 and, in aspects, are learned by the classifier 520 via a supervised procedure. In aspects, the feature vectors 522 are used with the corresponding activity labels 524 to train a conventional classifier. This classifier 520 may be any number of forms, including a random forest, neural network, logistic regression, support vector machine, and so forth. The classifier 520 is trained to estimate the activity label 528.

It will be appreciated that the steps in the second mode are effective to train the classifier 520 (to produce an entirely separate classifier) while keeping the networks 502 and 504 frozen. It is also possible to perform a fine-tuning on the trained networks 502 and 504 to estimate the activity classification, rather than train the classifier 520. One classifier can be used for wrist features and another for torso features. It is also possible that a classifier like classifier 520 can be trained using feature data from more than one sensor, and as such feature data from both networks 502 and 504 may be used as input to such a classifier, along with the activity labels 524; this approach contemplates activity recognition during monitoring mode (described below) where a human would wear the plurality of sensors at the same time, e.g., a chest patch sensor and a wrist sensor together.

In the monitoring mode, new accelerometer signals from a different human are processed to obtain feature vectors, then further processed to estimate the underlying activity class. More specifically, the trained wrist features neural network 504 is used with the trained classifier 520 to obtain classification of human activity. New accelerometer signals 530 from a monitored human subject are applied to the trained wrist features neural network 504 to produce features 532. The features 532 are applied to the trained classifier 520 to produce a classification 531 for the human activity in the signals 530. New accelerometer signals from torso sensors of a different human can be applied to the trained torso network to obtain feature vectors, which are applied to the trained classifier 520 to obtain an activity class.

Figure 6A:
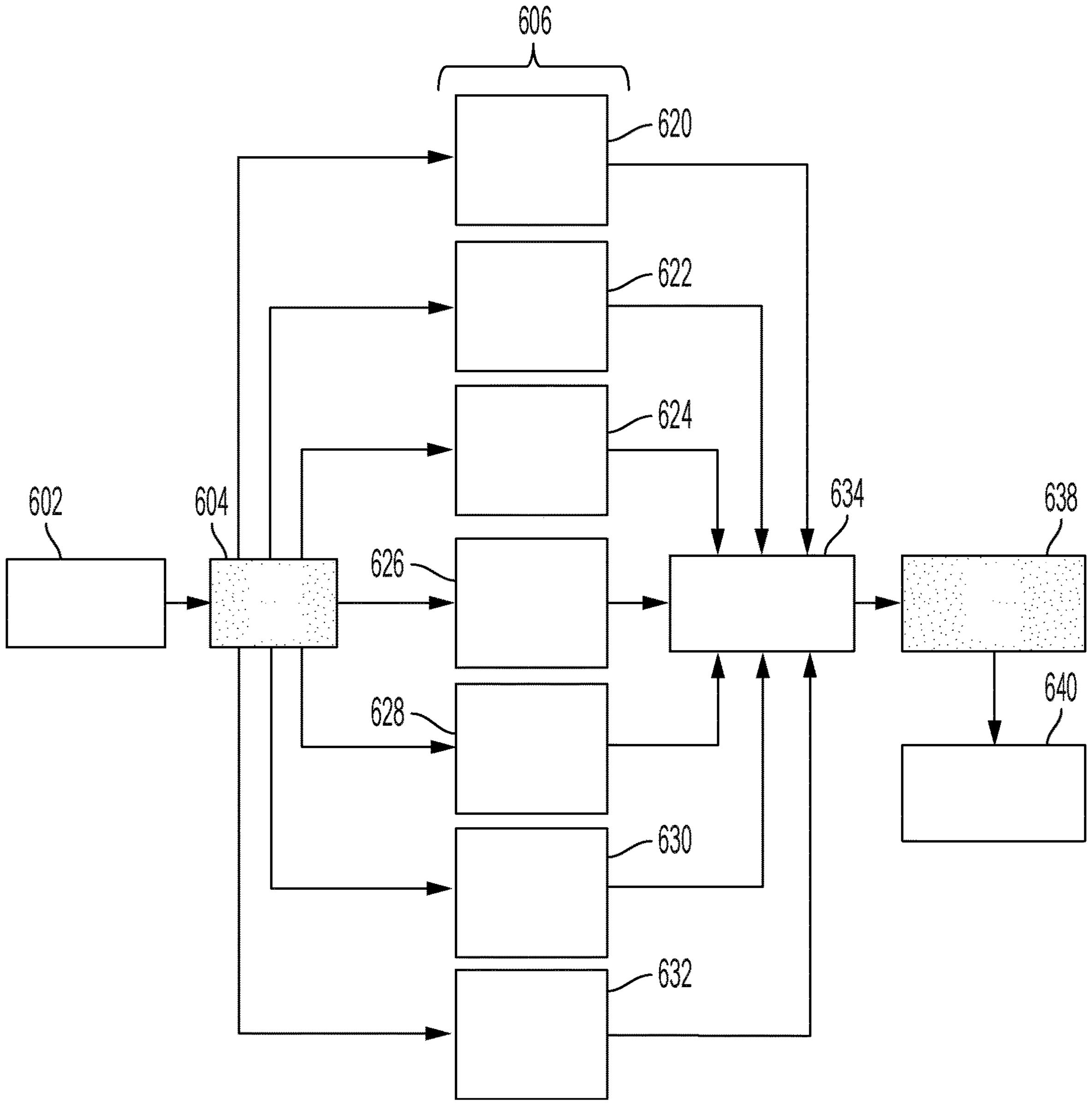
FIG. 6A comprises a diagram of a system as configured in accordance with various embodiments of these teachings.

Referring now to FIG. 6A, one example of the creation of a feature vector by a trained network is described. FIG. 6A shows accelerometer data 602 that is applied to a neural network 604 (e.g., the wrist or torso neural networks as described herein). Features 606 are produced and the features can be represented as vectors.

The features 606 are output (e.g., as vectors) over multiple time scales producing vectors 620, 622, 624, 626, 628, 630, and 632 so that the features capture both high level and low-level information about the underlying activity. In this implementation, the features represented by the vectors 620, 622, 624, 626, 628, 630, and 632 at each time scale are not the same shape and thus must be repeated to form a vector 634. The vector 634 is applied to a random forest 638 or other trained classifier to produce an activity classification 640.

The feature vector 620 represents 1 per second features and has a depth of 10. The feature vector 622 represents 1 per two second features and has a depth of 10. The feature vector 624 represents 1 per four second features and has a depth of 15. The feature vector 626 represents 1 per 8 second features and has a depth of 20. The feature vector 628 represents 1 per 15 second features and has a depth of 25. The feature vector 630 represents 1 per 30 second features and has a depth of 30. The feature vector 632 represents 1 per 60 second features and has a depth of 30. The depths are added (10+10+15+20+25+30+30) to achieve the 140 depth of the vector 634, and each one second time window has a vector 634.

In examples, the features of vector 620 are repeated such that each feature occurs at a once per second interval. For the once per second features, this means that no repetition occurs, while the once per minute features are repeated 60 times by feature vector 632. Overall, the vector 634 is produced and this is a 140-length feature vector for each 1 second of the 60 second accelerometer input.

Figure 6B:
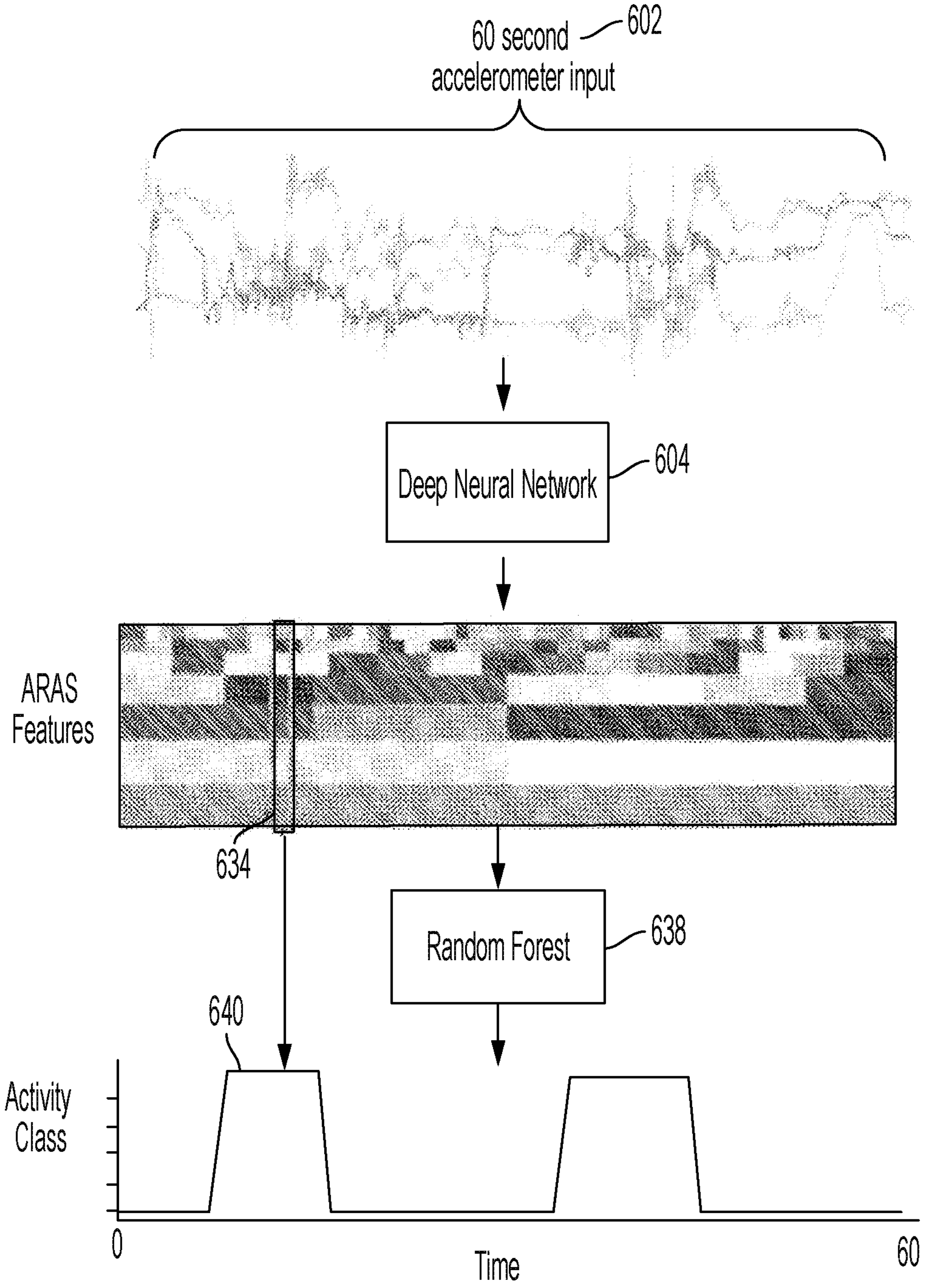
FIG. 6B comprises a diagram of a system as configured in accordance with various embodiments of these teachings.

Referring now to FIG. 6B, a diagram showing the monitoring mode is described. This process can be seen in the image of the monitoring mode steps below, in the features. The accelerometer data 602 is, in this example, 60 seconds of accelerometer input. This is applied to the neural network 604 to produce features in the form of vectors. Seven outputs (vectors 620, 622, 624, 626, 628, 630, and 632) are produced that each represent a different resolution of features at different time scales. These may be combined into an output vector 634, which is applied to the random forest 638 to produce an activity class determination. That is, the vector 634 is of length 140 and represents information across all time scales at a particular point in time to produce an activity classification 640. In this example, the activity classification is binary number with one value (e.g., 1) representing an activity (e.g., walking), while the other value (e.g., 0) represents another activity (e.g., resting). It will be appreciated that this is only one example of an activity classification and that other examples with more than two levels (i.e., having any number of levels) is possible.

Figure 7:
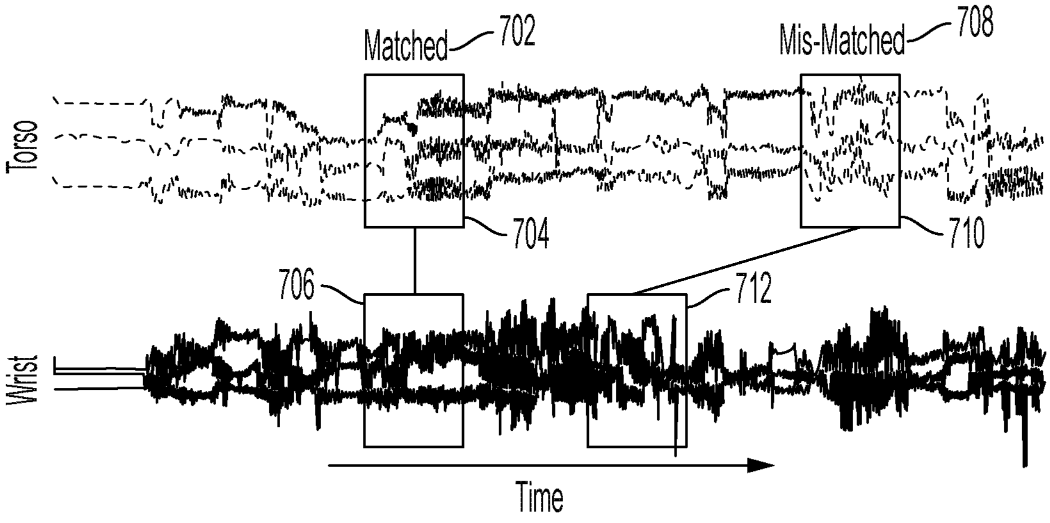
FIG. 7 comprises a diagram of a system as configured in accordance with various embodiments of these teachings.

Referring now to FIG. 7, one example of matched data and mis-matched data is shown. The matched and mismatched figure shows simultaneously collected data from a wrist accelerometer and a torso accelerometer and shows how paired segments of data are selected either during the same time period (matched), or during differing time periods (mis-matched).

It can be seen that matched data 702 includes torso sensor data 704 and wrist sensor data 706. The torso sensor data 704 and wrist sensor data 706 are taken from the exact same time or exact same time frame or period and would indicate the same activity of a human.

On the other hand, mis-matched data 708 includes torso sensor data 710 and wrist sensor data 712. The torso sensor data 710 and wrist sensor data 712 are not taken from the exact same time or exact same time frame or period and would not necessarily indicate the same activity of a human. Matched and mismatched pairs comprise data used to train the feature generating networks; "matched" and "mismatched" are effectively the labels used for that training. The class of the activity does not need to be known, nor even if the activities during mismatched inputs are in fact similar. The feature generating networks are trained to optimize chances that a comparison network can accurately predict matching. By generating features that do this, however, the features generated also become useful for improved classification of activity in the classifier.

Figure 8:
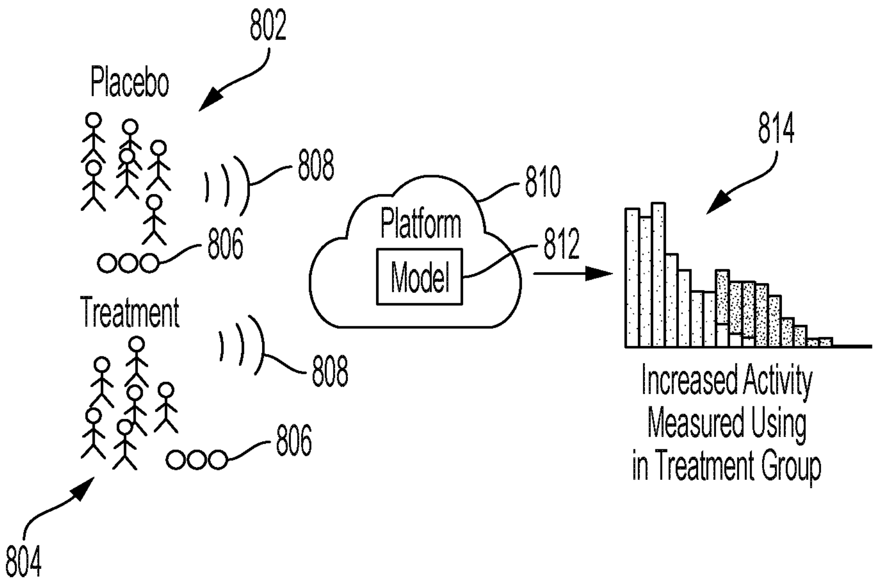
FIG. 8 comprises a diagram of one example of using these approaches in accordance with various embodiments of these teachings.

Referring now to FIG. 8, one example of an application of these approaches is described. In the example of FIG. 8, health effects between at least a control group receiving a first intervention or no intervention and a test group receiving a second intervention in a clinical trial are quantified.

A pharmaceutical company wants to show that a treatment can improve the quality of life of people suffering from heart failure. One group 802 received a treatment to address the illness, the other group 804 does not receive the treatment. Both groups are monitored using wrist-worn activity monitors or sensors 806. Accelerometer data 808 from the wrist devices 806 is streamed to the cloud 810 where the data is processed according to the approaches described herein, producing nuanced measurements of participants' activities. In these regards, the cloud 810 may include a platform with a control circuit, a memory, a trained neural network, and a trained classifier together referenced as a model 812. The accelerometer data 808 is applied to the trained neural network to produce feature vectors, and the feature vectors are applied to the trained classifier to produce an activity classification. The results can be depicted by graphs 814. Since the present approaches result in the creation of nuanced activity classifications, much more information is obtained concerning the underlying activity as compared to previous approaches.

At the end of the study, characteristics of activities are analyzed for each group. The enhanced detection capabilities using the present approaches, differences in attributes like walking speed, confidence of gait, and increased sit-to-stand occurrences can be shown and illustrated between the groups, indicating the new treatment's efficacy.

Other examples of using these approaches are possible and some are described below and utilize the cloud-based platform described above. In one additional example, a determination of possible health changes in the monitored human subject is made. For example, a patient is discharged from the hospital and is enrolled in a cloud-based platform where they are given a wrist worn activity monitor or sensor. The accelerometer data from the wrist device is streamed to the cloud-based platform, where the signals are automatically analyzed by the approaches described herein to produce activity classifications. The discharging clinician expects the patient to slowly increase their activity levels as they recover and monitors the activity classification produced by these approaches every day.

In other examples, an alert can be issued to a clinician to investigate the health of the monitored human subject. As an additional enhancement to the use case above (i.e., a discharge from hospital), the clinician sets an alert level for the recovering patient, where they wish to be alerted if the patient does not spend at least 20 minutes walking per day at least once in the week post hospital discharge. If the clinician receives the alert, they will contact the patient and suggest changes in their medical care.

In still other examples, these approaches can be used to selectively control the actuation or deactivation of a device. For example, the operation or setting a parameter of a medical device associated with treating or monitoring the monitored human subject can be performed. In one specific example, a patient with Parkinson's disease is enrolled in the cloud-based platform and is monitored using a wrist worn activity monitor. Data from the accelerometer is streamed to the cloud-based platform where it is analyzed according to the present approaches for signs of worsening tremors and gait patterns as indicated by the activity classifications that are obtained. If the system detects signs of worsening gait patterns, the patient's medication can be automatically adjusted to compensate. Medical monitoring devices can be adjusted or have their parameters altered. These devices can be controlled via electronic control signals created by the control circuits or other processing devices described herein.

In yet other examples, the operation or setting a parameter of a user electronic device associated with treating or monitoring the monitored human subject is controlled. For instance, a patient undergoing physical rehabilitation is enrolled in a platform and is monitored using a torso worn activity monitor. Data from the accelerometers are streamed to the platform where they are analyzed by the model, which shows if the patient is correctly performing the physical therapy activities. Based on the analysis, additional instructions or encouragement are pushed to the patient's mobile phone so they may perform the activity correctly. In aspects, graphics or icons on electronic device may be moved, controlled and/or altered so as to present these instructions or encouragement to the patient in specific patterns or ways.

Preferred embodiments of this disclosure are described herein, including the best mode known to the inventor(s). It should be understood that the illustrated embodiments are exemplary only and should not be taken as limiting the scope of the appended claims.

What is claimed is:

1. A method of determining and implementing appropriate life-improving actions for humans, the method comprising:
- iteratively training a first neural network to obtain a first trained neural network and a second neural network to obtain a second trained neural network by:
  - receiving a first set of wearable sensor data at the first neural network, the first neural network responsively producing a first feature vector, the first wearable sensor data describing first physiological features of a human, wherein any labels in the first set of wearable sensor data are ignored;
  - receiving a second set of second wearable sensor data at the second neural network, the second neural network responsively producing a second feature vector, the second wearable sensor data describing second physiological features of the human, wherein any labels in the second set of wearable sensor data are ignored;
  - wherein at least some of the first set of wearable sensor data and the second set of wearable sensor data are obtained from the same human activity of the same human occurring at the same time; and
  - predicting at a comparison neural network whether the first feature vector from the first neural network and the second feature vector from the second neural network are matched or mis-matched, the first feature vector and second feature vector determined to be matched when the first feature vector and the second feature vector are from the same human and taken at substantially the same time;
  - back propagating to the first neural network and the second neural network an error generated by a cost function that penalizes a failure to correctly determine whether the vectors are matched or mismatched, the backpropagation being effective to independently update parameters of the first neural network and the second neural network, to optimize a generation of features by the first neural network and the second neural network and to optimize prediction success of the comparison neural network;
- deploying the first trained neural network;
- monitoring a human subject to obtain current wearable sensor data and applying the current wearable sensor data to the first trained neural network to obtain a current feature vector;
- at a trained classifier, mapping the current feature vector to a classification representing one or more classes of activity; and
- based upon the classification, performing one or more actions selected from the group consisting of:
  - quantifying health affects between at least a control group receiving a first intervention and a test group receiving a second intervention in a clinical trial;
  - determining possible health changes in the monitored human subject;
  - issuing an alert to a clinician to investigate the health of the monitored human subject;

selectively controlling actuation or deactivation of a device;

controlling operation or setting a parameter of a medical device associated with treating or monitoring the monitored human subject; and controlling operation or setting a parameter of a user electronic device associated with treating or monitoring the monitored human subject.

2. The method of claim 1, wherein the mapping utilizes known and labeled vectors from other monitored human subjects.

3. The method of claim 1, wherein the sensors are wrist sensors or chest sensors.

4. The method of claim 1, wherein the user electronic device is a smartphone, a personal computer, a laptop, or a tablet.

5. The method of claim 1, wherein the trained classifier comprises a random forest or a third neural network.

6. The method of claim 1, wherein the first neural network, second neural network are trained at a central location.

7. The method of claim 1, wherein said comparison network comprises an ensemble of separate comparison networks with different time scales of a fixed input window size.

8. A system of determining and implementing appropriate life-improving actions for humans, the system comprising:

a first neural network;

a second neural network;

a comparison neural network coupled to the first neural network and the second neural network;

wherein the first neural network is configured to receive a first set of wearable sensor data, the first neural network responsively producing a first feature vector, the first clinical data describing first physiological features of a human, wherein any labels in the first set of wearable sensor data are ignored;

wherein the second neural network is configured to receive a second set of wearable sensor data, the second neural network responsively producing a second feature vector, the second wearable sensor data describing second physiological features of the human, wherein any labels in the second set of wearable sensor data are ignored;

wherein at least some of the first set of wearable sensor data and the second set wearable sensor data are obtained from the same human activity of the same human occurring at the same time; and wherein the comparison neural network is configured to predict whether the first feature vector from the first neural network and the second feature vector from the second neural network are matched or mis-matched, the first feature vector and second feature vector determined to be matched when the first feature vector and the second feature vector are from the same human and taken at substantially the same time;

wherein an error is back propagated to the first neural network and the second neural network, the error generated by a cost function that penalizes a failure to correctly determine whether the vectors are matched or mis-matched, the back propagation being effective to independently update parameters of the first neural network and the second neural network to produce a first trained neural network and a second trained neural network;

wherein the system further comprises a trained classifier and wearable sensors, the wearable sensors being worn by a current human subject;

wherein the first trained neural network is deployed and current wearable sensor data is obtained from the current human subject by the wearable sensors and applied to the first trained neural network to obtain a current feature vector; and wherein at the trained classifier, the current feature vector is mapped to a classification representing one or more classes of activity and based on the classification, one or more actions are performed, the actions selected from the group consisting of:

quantifying health affects between at least a control group receiving a first intervention and a test group receiving a second intervention in a clinical trial;

determining possible health changes in the current human subject;

issuing an alert to a clinician to investigate the health of the current human subject;

selectively controlling actuation or deactivation of a device;

controlling operation or setting a parameter of a medical device associated with treating or monitoring the current human subject; and controlling operation or setting a parameter of a user electronic device associated with treating or monitoring the current human subject.

9. The system of claim 8, wherein the mapping utilizes known and labeled vectors from other human subjects.

10. The system of claim 8, wherein the wearable sensors are wrist sensors or chest sensors.

11. The system of claim 8, wherein the trained first neural network is deployed at a central location.

12. The system of claim 8, wherein the training occurs at a central location.

13. The system of claim 8, wherein the trained classifier comprises a random forest or a third neural network.

14. A system for training neural networks, the system comprising:

a first neural network;

a second neural network;

a comparison neural network coupled to the first neural network and the second neural network;

a control circuit coupled to the first neural network, the second neural network, and the comparison neural network, the control circuit configured to:

obtain a first collection of samples of wearable sensor data from a plurality of humans with a first type of wearable sensor;

obtain a second collection of samples of wearable sensor data from a plurality of humans with a second type of wearable sensor, at least some of said samples being matched to the same human and substantially the same time-window as samples of said first collection; and train the first neural network to produce a first trained neural network by iteratively:

inputting samples from said first collection to said first neural network to generate features;

inputting samples from said second collection to a second neural network to generate features;

inputting features from said first neural network together with features from said second neural network to the comparison neural network that responsively predicts whether input samples were matched or mis-matched; and back propagating to the first neural network and the second neural network an error generated by a cost function that penalizes failure to correctly determine whether the input samples are matched or mis-matched, to change neural parameters of the first neural network and the second neural network independently, to optimize generation of features by the first neural network and by the second neural network that optimize prediction success of the comparison neural network.

15. The system of claim 14, further comprising a trained classifier and:

wherein the first trained neural network is subsequently deployed and wearable sensor data from a monitored human subject is captured;

wherein the wearable sensor data is applied to the first neural network and the first neural network responsively generates a set of features responsive to a time-window of the wearable sensor data, wherein the trained classifier maps the generated features to one or more classes of activity in said time-window; and wherein based on said classification, one or more actions are performed, the actions being selected from the group consisting of:

quantifying health affects between at least a control group receiving a first intervention and a test group receiving a second intervention in a clinical trial;

determining possible health changes in the monitored human subject;

issuing an alert to a clinician to investigate the health of the monitored human subject;

selectively controlling actuation or deactivation of a device;

controlling operation or setting a parameter of a medical device associated with treating or monitoring the monitored human subject; and controlling operation or setting a parameter of a user electronic device associated with treating or monitoring the monitored human subject.

16. The system of claim 15, wherein the sensors are wrist sensors or chest sensors.

17. The system of claim 15, wherein the trained classifier comprises a random forest or a third neural network.

18. The system of claim 15, wherein the training occurs at a central location.

19. A method of training a neural network, the method comprising:

obtaining a first collection of samples of wearable sensor data from a plurality of humans with a first wearable sensor;

obtaining a second collection of samples of wearable sensor data from a plurality of humans with a second wearable sensor, at least some of said samples being matched to the same human and substantially the same time-window as samples of said first collection; and training a first neural network to produce a first trained neural network by iteratively:

inputting samples from said first collection to said first neural network to generate features;

inputting samples from said second collection to a second neural network to generate features;

inputting features from said first neural network together with features from said second neural network to a comparison network that predicts whether input samples were matched or mis-matched; and back propagating to said first neural network and said second neural network an error generated by a cost function that penalizes failure to correctly determine whether the input samples are matched or mis-matched, to update neural parameters of said first neural network and said second neural network independently, to improve generation of features by said first neural network and by said second neural network that improve prediction success of said comparison neural network.

20. The method of claim 19, further comprising:

deploying the first trained neural network, capturing wearable sensor data from a monitored human subject;

applying the captured wearable sensor data to the first trained neural network, and by the first trained neural network, generating a set of features responsive to a time-window of the captured wearable sensor data, and by a trained classifier, mapping the generated features to one or more classes of activity in the time-window; and based on said classification, performing one or more actions selected from the group consisting of:

quantifying health affects between at least a control group receiving a first intervention and a test group receiving a second intervention in a clinical trial;

determining possible health changes in the monitored human subject;

issuing an alert to a clinician to investigate the health of the monitored human subject;

selectively controlling actuation or deactivation of a device;

controlling operation or setting a parameter of a medical device associated with treating or monitoring the monitored human subject; and controlling operation or setting a parameter of a user electronic device associated with treating or monitoring the monitored human subject.

21. The method of claim 20, wherein the first wearable sensor and the second wearable sensor are wrist sensors or chest sensors.

22. The method of claim 20, wherein the trained classifier comprises a random forest or a third neural network.

23. The method of claim 20, wherein the training occurs at a central location.

24. A method, the method comprising:

capturing wearable sensor data from a monitored human subject;

by a first neural network, generating a set of features responsive to a time-window of the wearable sensor data;

by a trained classifier, mapping said generated set of features to one or more classes of activity in said time-window;

and based on the classes of activity, performing one or more actions selected from the group consisting of:

quantifying health affects between at least a control group receiving a first intervention and a test group receiving a second intervention in a clinical trial;

determining possible health changes in the monitored human subject;

issuing an alert to a clinician to investigate the health of the monitored human subject;

selectively controlling actuation or deactivation of a device;

controlling operation or setting a parameter of a medical device associated with treating or monitoring the monitored human subject; and controlling operation or setting a parameter of a user electronic device associated with treating or monitoring the monitored human subject;

wherein said first neural network is created by:

obtaining a first collection of samples of wearable sensor data from a plurality of humans with a first type of wearable sensor;

obtaining a second collection of samples of wearable sensor data from a plurality of humans with a second type of wearable sensor, at least some of said samples being matched to the same human and substantially the same time-window as samples of said first collection;

training said first neural network by iteratively:

inputting samples from said first collection to said first neural network to generate features;

inputting samples from said second collection to a second neural network to generate features;

inputting features from said first neural network together with features from said second neural network to a comparison network that predicts whether input samples were matched or mis-matched; and back propagating to said first neural network and said second neural network an error generated by a cost function that penalizes failure to correctly determine whether the input samples are matched or mis-matched, to update neural parameters of said first neural network and said second neural network independently, to improve generation of features by said first neural network and by said second neural network that improve prediction success of said comparison neural network.

25. The method of claim 24, wherein the wearable sensor data is obtained from wrist sensors or chest sensors.

26. The method of claim 24, wherein the trained classifier comprises a random forest or a third neural network.

27. The method of claim 24, wherein the training occurs at a central location.

* * * * *